(12) United States Patent
Artis et al.

(10) Patent No.: US 7,265,146 B2
(45) Date of Patent: Sep. 4, 2007

(54) INTEGRIN RECEPTOR INHIBITORS

(75) Inventors: Dean R. Artis, Kensington, CA (US); David Y. Jackson, San Bruno, CA (US); Thomas E. Rawson, Mountain View, CA (US); Mark E. Reynolds, Millbrae, CA (US); Daniel P. Sutherlin, South San Francisco, CA (US); Mark S. Stanley, Pacifica, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 11/111,105

(22) Filed: Apr. 20, 2005

(65) Prior Publication Data

US 2005/0187284 A1 Aug. 25, 2005

Related U.S. Application Data

(63) Continuation of application No. 10/676,706, filed on Sep. 30, 2003, now Pat. No. 6,933,314, which is a continuation of application No. 10/313,147, filed on Dec. 6, 2002, now Pat. No. 6,706,753, which is a continuation of application No. 09/932,695, filed on Aug. 16, 2001, now abandoned.

(60) Provisional application No. 60/226,626, filed on Aug. 18, 2000.

(51) Int. Cl.
*A61K 31/403* (2006.01)
*C07D 207/04* (2006.01)
*C07D 209/82* (2006.01)

(52) U.S. Cl. ............... 514/411; 548/427; 548/439; 548/440; 548/444; 548/530; 548/537; 548/538; 514/408; 514/423

(58) Field of Classification Search ............ 548/427, 548/439, 440, 444, 530, 537, 538; 514/411, 514/908, 423
See application file for complete search history.

(56) References Cited

U.S. PATENT DOCUMENTS

| | | | |
|---|---|---|---|
| 5,079,260 A | 1/1992 | Weitzberg et al. | |
| 5,223,517 A | 6/1993 | Muller et al. | |
| 5,272,161 A | 12/1993 | Niewohner et al. | |
| 5,334,606 A | 8/1994 | MacLeod | |
| 5,519,043 A | 5/1996 | Perumattam | |
| 5,773,465 A | 6/1998 | Gandolfi et al. | |
| 5,773,646 A | 6/1998 | Chandrakumar et al. | |
| 5,891,899 A | 4/1999 | Clark et al. | |
| 5,908,863 A | 6/1999 | Allegretti et al. | |
| 5,994,351 A | 11/1999 | Robinson et al. | |
| 6,706,753 B2* | 3/2004 | Artis et al. | 514/422 |
| 6,933,314 B2* | 8/2005 | Artis et al. | 514/411 |

FOREIGN PATENT DOCUMENTS

| | | |
|---|---|---|
| EP | 327877 | 8/1989 |
| JP | 48054061 | 7/1973 |
| WO | WO97/01540 | 1/1997 |
| WO | WO99/10312 | 3/1999 |

OTHER PUBLICATIONS

Andrew, H. F., et al., "Nitration of 3-Methylfluoranthene" *J. Chem. Soc.*, Perkins Trans. 1 vol. 6:755-759 (1972).
Butcher et al., "Lymphocyte Homing and Homeostasis" *Science* 272:60-66 (1996).
Cardarelli et al., "Cyclic RGD Peptide Inhibits α4β1 Interaction with Connecting Segment 1 and Vascular Cell Adhesion Molecule" *Journal of Biological Chemistry* 269:18668-18673 (1994).
Chuluyan et al., "α4—Integrin-dependent emigration of monocytes" *Springer Semin. Immunopathology* 16:391-404 (1995).
Database Crossfire Beilstein 'Online', Beilstein Institut zur Forderung der Chemischen Wissenschafte, Frankfurt am Main, DE; Database accession No. 2187180 XP002194815 Abstract; & Campell, Crombie: Proc. Royal Soc. London, Series A, Mathematical & Physical Sciences, 65:376 (1960-1961) Royal Society of.
Elices et al., "VCAM-1 on activated endothelium interacts with the leukocyte integrin VLA-4 at a site distinct from the VLA-4/fibronectin binding site" *Cell* 60:577-584 (1990).
Fotouhi et al., "Cyclic Thioether Peptide Mimetics as VCAM-VLA-4 Antagonists" *Bioorganic & Medicine Chemistry Letters* 10:1167-1169 (2000).
Hamilton, et al., "Fluorenylalkanoic and Benzoic Acids as Novel Inhibitors of Cell Adhesion Processes in Leukocytes" *J. Med. Chem.* 38:1650-1656 (1995).
Hemler, "VLA proteins in the integrin family: structures, functions, and their role on leukocytes" *Annu. Rev. Immunol.* 8:365-400 (1990).
Hynes, "Integrins: versatility, modulation, and signaling in cell adhesion" *Cell* 69(1) :11-25 (1992).

(Continued)

*Primary Examiner*—Golam M. M. Shameem
(74) *Attorney, Agent, or Firm*—David W Evans

(57) ABSTRACT

Provided are compounds of formula (I)

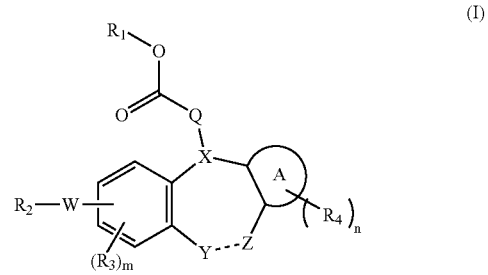

wherein A, Q, W, X, Y, Z, $R_1$ to $R_4$, m and n are as defined herein. Compounds of the invention bind to $\alpha_4$ integrin receptors and thereby inhibit binding of ligands for $\alpha_4$ integrins which is useful for prophylactic and/or therapeutic treatment of diseases and conditions associated with $\alpha_4$ integrins or their ligands.

17 Claims, No Drawings

OTHER PUBLICATIONS

Jackson et al., "Potent α4β1 Peptide Antagonists as Anti-Inflammatory Agents" *Journal of Medicinal Chemistry* 40 (21) :3359-3368 (Oct. 10, 1997).

Juliano et al., "Adhesion molecules in cancer: the role of integrins" *Current Opinion Cell Biology* 5:812-818 (1993).

Laberge, S. et al., "Role of VLA-4 and LFA-1 in Allergen-Induced Airway Hyperrespnosiveness and Lung Inflammation in the Rat" *Am. J. Respir. Crit. Care Med.* 151:822-829 (1995).

Makarem et al., "Competitive binding of vascular cell adhesion molecule-1 and the HepII/IIICS domain of fibronectin to the integrin α4β1" *Journal of Biological Chemistry* 269:4005-4011 (1994).

Nakajima et al., "Role of vascular cell adhesion molecule 1/very late activation antigen 4 and intercellular adhesion molecule 1/lymphocyte function-associated antigen 1 interactions in antigen—induced eosinophil and T cell recruitment into the tissue" *Journal of Experimental Medicine*.

Sharar et al., "The adhesion cascade and anti-adhesion therapy: an overview" *Springer Semin. Immunopathology* 16:359-378 (1995).

Simmons et al., "Vascular cell adhesion molecule-1 expressed by bone marrow stromal cells mediates the binding of hematopoietic progenitor cells" *Blood* 80:388-395 (1992).

\* cited by examiner

INTEGRIN RECEPTOR INHIBITORS

FIELD OF THE INVENTION

The present invention relates to novel compounds useful as therapeutic, prophylactic or diagnostic agents having binding affinity to integrin receptors, in particular to $\alpha_4$ integrins.

BACKGROUND OF THE INVENTION

The integrins are $\alpha/\beta$ heterodimeric cell surface receptors involved in numerous cellular processes from cell adhesion to gene regulation (Hynes, Cell 1992, 69, 11-25; Hemler, Annu. Rev. Immunol. 1990, 8, 365-368). Several integrins have been implicated in disease processes and have generated widespread interest as potential targets for drug discovery (Sharar et al, Springer Semin. Immunopathology 1995, 16, 359-378). In the immune system, integrins are involved in leukocyte trafficking, adhesion and infiltration during inflammatory processes (Nakajima et al, J. Exp. Med. 1994, 179, 1145-1154).

Differential expression of integrins regulates the adhesive properties of cells and different integrins are involved in different inflammatory responses (Butcher et al, Science 1996, 272, 60-66). The $\alpha_4$ integrins, $\alpha_4\beta_1$ (VLA-4) and $\alpha_4\beta_7$ (LPAM), are expressed primarily on monocytes, lymphocytes, eosinophils, basophils, and macrophages but not on neutrophils (Elices et al, Cell 1990, 60, 577-584). The primary ligands for $\alpha_4$ integrins are the endothelial surface proteins mucosal addressin cell adhesion molecule (MAd-CAM) and vascular cell adhesion molecule (VCAM) with lower affinity (Makarem et al, J. Biol. Chem. 1994, 269, 4005-4011). The binding of the $\alpha_4\beta_1$ or $\alpha_4\beta_7$ to MAdCAM and/or VCAM expressed on high endothelial venules (HEVs) at sites of inflammation results in firm adhesion of the leukocyte to the endothelium followed by extravasation into the inflamed tissue (Chuluyan et al, Springer Semin. Immunopathology 1995, 16, 391-404). Monoclonal antibodies directed against $\alpha_4\beta_1$, $\alpha_4\beta_7$, MAdCAM or VCAM have been shown to be effective modulators in animal models of chronic inflammatory diseases such as asthma (Simmons et al, Blood 1992, 80, 388-395), rheumatoid arthritis (RA) (Juliano et al, Current Opinion Cell Biology 1993, 5, 812-818), and inflammatory bowel diseases (IBD) (Laberge et al, Am. J. Respir. Crit Care Med. 1995, 151, 822-829 and Barbadillo et al, Springer Semin. Immunopathology 1995, 16). While antibodies have shown efficacy they must be administered parenterally and are inherently cumbersome to produce.

Accordingly, it would be desirable to provide small molecule compounds which inhibit the interaction between $\alpha_4$ integrins and ligands MAdCAM and/or VCAM which would be useful for treatment of chronic inflammatory diseases such as arthritis, asthma, multiple sclerosis, Chrohn's disease, ulcerative colitis, and hepatitis C.

SUMMARY OF THE INVENTION

According to an aspect of the present invention there is provided compounds of formula (I)

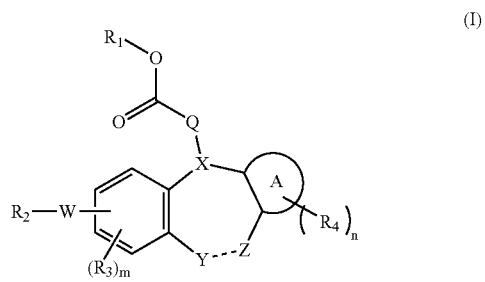

wherein
A is a 5 or 6 member, saturated or unsaturated carbocycle or heterocycle optionally substituted by oxo and $R_4$;
Q is alkyl, alkenyl or alkynyl optionally substituted with halogen, carboxyl, alkyl or aryl, and wherein one or more carbon atoms are optionally replaced with O, N, $NR_6$, S, SO, or $SO_2$;
X is —$CR_5$— or —N—;
Y is H, —$CHR_3$—, —$CR_3$=, or a bond;
Z is H, —$CHR_3$—, =$CR_3$—, —$NR_3$—, =N—, O, S, SO, $SO_2$ or a bond, provided that when one of Y and Z is H then the other is also H;
W is —C(O)$NR_6$—, —$NR_6$C(O)—, —C(S)$NR_6$—, —$NR_6$C(S)—, $NR_6$, O, S, $SO_2$, —$CH_2$—, —C—, —$NR_6SO_2$—, —$SO_2NR_6$—, —OC(O)$NR_6$—, —$NR_6$C(O)O—, —OC(S)$NR_6$—, —$NR_6$C(S)O—, —S—C(S)$NR_6$—, —C(O)—, —$NR_6$C(O)$NR_6$— or —$NR_6$C(S)$NR_6$—;
$R_1$ is hydrogen or is selected from the group consisting of alkyl, alkenyl and alkynyl, each of which is optionally substituted with hydroxyl, halogen, amino, nitro, carboxyl, a carbocycle, or a heterocycle; or $R_1$ is a carbocycle or heterocycle optionally substituted with hydroxyl, oxo, halogen, amino, or nitro;
$R_2$ is selected from the group consisting of alkyl, alkenyl and alkynyl, each of which is optionally substituted with halogen, hydroxyl, oxo alkoxy, amino, nitro, carboxyl, carboxamido, acyl, acyloxy, amidinyl, guanidinyl, thiol, alkylthio, or one or more carbocycle or heterocycle optionally substituted with halogen, hydroxyl, oxo, alkoxy, amino or carboxyl; or $R_2$ is a carbocycle or heterocycle optionally substituted with halogen, hydroxyl, oxo, alkoxy, amino, nitro, carboxyl, acyl, acyloxy, alkyl, alkenyl, alkynyl or a carbocycle or heterocycle optionally substituted with halogen, hydroxyl, oxo, alkoxy, amino or carboxyl;
$R_3$ and $R_4$ are independently selected from the group consisting of H, hydroxyl, halogen, amino, nitro, carboxyl, alkyl, alkenyl, alkynyl, a carbocycle and a heterocycle, wherein said alkyl, alkenyl, alkynyl, carbocycle and heterocycle groups are optionally substituted with one or more substituents selected from the group consisting of hydroxyl, halogen, amino, oxo and carboxyl, and optionally one or more carbon atoms of said alkyl, alkenyl and alkynyl group is replaced with N, $NR_6$, O, S, SO or $SO_2$;
$R_5$ is H or alkyl, alkenyl or alkynyl optionally having a carbon atom replaced with O, N or $NR_6$, and optionally substituted with $COOR_1$; or $R_5$ together with the carbon atom from which it depends forms a double bond to an adjacent carbon or nitrogen atom of Q; or $R_5$ together with a non-adjacent carbon or nitrogen atom of Q form a carbocycle or heterocycle;

$R_6$ is hydrogen, alkyl, alkenyl or alkynyl;

m and n are independently 1, 2 or 3;

and salts, solvates and hydrates thereof.

In another aspect of the invention, there is provided pharmaceutical compositions comprising a compound of the invention and a pharmaceutically acceptable carrier, excipient or adjuvant.

In another aspect of the invention, there is provided a method of inhibiting binding of an $\alpha_4$ integrin to a protein ligand comprising contacting said $\alpha_4$ integrin with a compound of the invention.

In another aspect of the invention, there is provided a method of treating a disease or condition mediated by $\alpha_4$ integrin receptors or ligands of $\alpha_4$ integrin receptors in a mammal, the method comprising administering to said mammal an effective amount of a compound of the invention.

DETAILED DESCRIPTION OF THE INVENTION

Compounds are provided having binding affinity for $\alpha_4$ integrins, having the general formula (I)

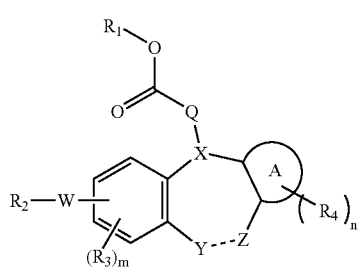

(I)

wherein A, Q, W, X, Y, Z, $R_1$ to $R_4$, m and n are as defined herein.

Ring A is a 5 or 6 member, saturated or unsaturated carbocycle or heterocycle optionally substituted by oxo (=O) and $R_4$. By "carbocycle" is meant herein to be a mono- bi- or tricyclic ring system containing a 4-16 carbon atom scaffold that is saturated, partially unsaturated or fully unsaturated including aromatic. In the context of ring A, suitable carbocycles include cycloalkyl, cycloalkenyl and aryl. In a preferred embodiment, ring A is a carbocycle selected from the group consisting of cyclopentyl, cyclohexyl and benzene. In a most preferred embodiment ring A is benzene. In another embodiment, ring A is a heterocycle. By "heterocycle" is meant herein to be a mono-, bi- or tricyclic ring system comprising a combination of 4-16 carbon and hetero atoms (i.e. N, O, and S, as well as SO and $SO_2$) that is saturated, partially unsaturated or fully unsaturated including aromatic. In the context of ring A, preferred heterocycles are 5 and 6 member monocycles. Particularly preferred ring A heterocycles include pyridine, pyran, pyrimidine, pyrazine, pyridazine, pyrole, furan, thiophene, imidazole, pyrazole, thiazole and triazole. It is appreciated that ring A encompasses heterocycles in which the heteroatoms may be shared with the central ring, if present, and/or may be adjacent to X.

Q is a divalent alkyl, alkenyl or alkynyl linking group optionally substituted with halogen, carboxyl, alkyl or aryl, and wherein one or more carbon atoms are optionally replaced with O, N, $NR_6$, S, SO, or $SO_2$. In a preferred embodiment, Q is alkyl having 1 to 3 carbon atoms or methylene groups in length, and more preferably length of 2 methylene groups. In another preferred embodiment, the methylene group adjacent to the group X is replaced with a nitrogen atom or $NR_6$ and more preferably with an oxygen atom. In a particularly preferred embodiment, Q is —O—$CH_2$— wherein the oxygen atom is adjacent to the X group.

X is a bridging group —$CR_5$— or —N— from which the group Q depends. In a preferred embodiment, X is —$CR_5$— wherein $R_5$ is H. In another embodiment $R_5$ is alkyl, alkenyl or alkynyl optionally having a carbon atom replaced with O, N or $NR_6$, and is optionally substituted with $COOR_1$. By "alkyl", "alkenyl" and "alkynyl" is meant herein to be straight or branched aliphatic groups having 1-10 carbon atoms, preferably 1-6 and more preferably 1-4. Preferred alkyl groups are methyl, ethyl, propyl, i-propyl, n-butyl, i-butyl, s-butyl and t-butyl. Preferably, $R_5$ is an alkyl group having 1 to 3 carbon atoms or methylene groups in length and is substituted with $COOR_1$. More preferably, $R_5$ is —$(CH_2)_2$—$COOR_1$. In another embodiment, $R_5$ together with the carbon atom from which it depends forms a double bond to an adjacent carbon or nitrogen atom of Q. In yet another embodiment $R_5$ together with a non-adjacent carbon or nitrogen atom from the group Q form a carbocycle or heterocycle. In this context, a preferred embodiment is when $R_5$ and the carbon atom in Q which is beta to the group X form a 1,3-dioxolane ring. In a particularly preferred embodiment, the dioxolane ring is spiro at X and the two oxygen atoms are alpha to the X group.

Y is H, —$CHR_3$—, —$CR_3$=, or a bond and Z is H, —$CHR_3$—, =$CR_3$—, —$NR_3$—, =N—, O, S, SO, $SO_2$ or a bond, provided that when one of Y and Z is H then the other is also H. In a preferred embodiment, one of Y and Z is a bond while the other is —$CHR_3$— thereby forming a six member ring fused to ring A and the benzene ring of formula (I) resulting in a tricyclic ring system. In another preferred embodiment Y and Z are both —$CHR_3$— thereby forming a seven member ring. In a more preferred embodiment, Y and Z are both H wherein ring A and the benzene ring of formula (I) are linked via group X rather than forming a fused tricyclic ring system. In a more preferred embodiment, Y and Z are both a bond thereby forming a five member ring fused to ring A and the benzene ring, and in a most preferred embodiment the five member ring together with ring A and the benzene ring of formula (I) form a fluorenyl ring.

W is —C(O)$NR_6$—, —$NR_6$C(O)—, —C(S)$NR_6$—, —$NR_6$C(S)—, $NR_6$, O, S, $SO_2$, —$CH_2$—, —C—, —$NR_6SO_2$—, —$SO_2NR_6$—, —OC(O)$NR_6$—, —$NR_6$C(O)O—, —OC(S)$NR_6$—, —$NR_6$C(S)O—, —S—C(S)$NR_6$—, —C(O)—, —$NR_6$C(O)$NR_6$— or —$NR_6$C(S)$NR_6$—. In a particular embodiment W is the amido group —C(O)$NR_6$— wherein the nitrogen atom is adjacent to the benzene ring of formula (I), or alternatively —$NR_6$C(O)— wherein the carbonyl is adjacent to the benzene ring. In another particularly embodiment W is the sulfonamido group —$NR_6SO_2$— wherein the sulfur atom is adjacent to the benzene ring, or alternatively —$SO_2NR_6$— wherein the nitrogen atom is adjacent to the benzene ring. In the context where W is amido or sulfonamido, $R_6$ is preferably H or $C_{1-4}$ alkyl and more preferably H or methyl. In another particular embodiment, W is O. In a particularly preferred embodiment W is $NR_6$ wherein $R_6$ is H or $C_{1-4}$ alkyl and particularly H or methyl.

R₁ is hydrogen or is selected from the group consisting of alkyl, alkenyl and alkynyl, each of which is optionally substituted with hydroxyl, halogen, amino, nitro, carboxyl, a carbocycle, or a heterocycle. By "amino" is meant herein to be a primary, secondary or tertiary amine substituted with alkyl, alkenyl, alkynyl, aryl, or aralkyl each optionally substituted as provided herein. By "carboxyl" is meant herein to be —COOH as well as carboxy ester groups thereof and in particular alkyl esters thereof. Alternatively R₁ is a carbocycle or heterocycle optionally substituted with hydroxyl, oxo, halogen, amino, or nitro. In a preferred embodiment R₁ is H or a group which is liberated in vivo to yield a free carboxy group —C(O)O⁻.

R₂ is selected from the group consisting of alkyl, alkenyl and alkynyl, each of which is optionally substituted with halogen, hydroxyl, oxo (═O), alkoxy, amino, nitro, carboxyl, carboxamido, acyl, acyloxy, amidinyl (—C(NH)NH— or —NHC(NH)—), guanidinyl (—NHC(NH)NH—), thiol, alkylthio, or one or more carbocycle or heterocycle optionally substituted with halogen (F, Cl, Br or I), hydroxyl, oxo, alkoxy, amino or carboxyl. By "alkoxy" is meant herein to include —O-alkyl, —O-alkenyl and —O-alkynyl wherein alkyl, alkenyl and alkynyl are as previously defined. By "acyl" is meant herein to be a substituted carbonyl (—C(O)—). Suitable acyl groups include alkanoyl, aroyl and aralkanoyl. Suitable acyloxy groups include alkanoyloxy, aroyloxy and aralkanoyloxy. In a particularly preferred embodiment R₂ is a naturally occurring or non-naturally occurring D or L-amino acid residue in which the alpha nitrogen or alpha amino group is optionally acylated. In particularly preferred embodiments, W is NR₆ and R₂ is N-acetyl-tyrosine, D-tyrosine, phenylalanine, benzoyl, isonipecotoyl, 4-methoxyphenylacetyl, 1-fluorenyl-carbonyl, 1-naphthoyl, 2-naphthoyl, 3-hydroxy-phenylalanine, 3-iodo-tyrosine, 3-fluoro-tyrosine, 3-chloro-tyrosone, 4-(4-hydroxyphenyl)-benzoyl, 2,3,5,6-tetrafluoro-tyrosine, 6-hydroxynaphthoyl, 2-phenyl-3-(4-hydroxyphenyl)propanoyl and N-acetyl-3-(4-hydroxyphenyl)proline. In a more preferred embodiment R₂ is a tyrosine amino acid reside and more preferably a tyrosine residue wherein the alpha nitrogen is acylated with acetyl (i.e. N-acetyl tyrosine).

In another embodiment R₂ is a carbocycle or heterocycle optionally substituted with one or more halogen, hydroxyl, oxo, alkoxy, amino, nitro, carboxyl, acyl, acyloxy, alkyl, alkenyl, alkynyl or a carbocycle or heterocycle optionally substituted with halogen, hydroxyl, oxo, alkoxy, amino or carboxyl. In a particular embodiment R₂ is a heterocycle substituted with a phenyl group which in turn is optionally substituted with one or more halogen, hydroxyl, alkoxy or carboxyl. In a particularly preferred embodiment, the heterocycle is a pyrrolidine ring such that when W is an amido group —C(O)NR₆— or —NR₆C(O)—R₂ and W together form a proline amino acid residue. The proline residue is preferably substituted at its beta carbon (i.e. 3-position of the pyrrolidine ring) with a phenyl group which is optionally para-substituted (i.e at its 4-position) with hydroxyl thereby forming a constrained tyrosine residue. The phenyl group is optionally substituted at one or more of the 2, 3, 5 and 6 positions with a halogen, in particular iodo (I), chloro (Cl) or fluoro (I). Further, the nitrogen atom of the proline residue is optionally acylated, in particular with an alkanoyl group such as acetyl.

R₃ and R₄ are independently selected from the group consisting of H, hydroxyl, halogen, amino, nitro, carboxyl, alkyl, alkenyl, alkynyl, a carbocycle and a heterocycle, wherein said alkyl, alkenyl, alkynyl, carbocycle and heterocycle groups are optionally substituted with one or more substituents selected from the group consisting of hydroxyl, halogen, amino, oxo and carboxyl, and optionally one or more carbon atoms of said alkyl, alkenyl and alkynyl group is replaced with N, NR₆, O, S, SO or SO₂. In a particular embodiment R₃ and R₄ are H. Alternatively, one or both of R₃ and R₄ are a carboxy group —COOR₁ linked to the ring from which it depends via a linking group such as an alkyl chain of 1-6 methylene groups in length and preferably 1-3 methylene groups. The linking group may depend from the ring by a functional group such as O (alkoxy), NR₆ (amino), an amido group or a sulfonamido group. In a preferred embodiment, both 'm' and 'n' are the integer 1.

R₆ is hydrogen, alkyl, alkenyl or alkynyl. In a preferred embodiment R₆ is C₁₋₄ alkyl and more preferably methyl. In another more preferred embodiment R₆ is H.

In accordance with a preferred embodiment, compounds of the invention have the general formula (II):

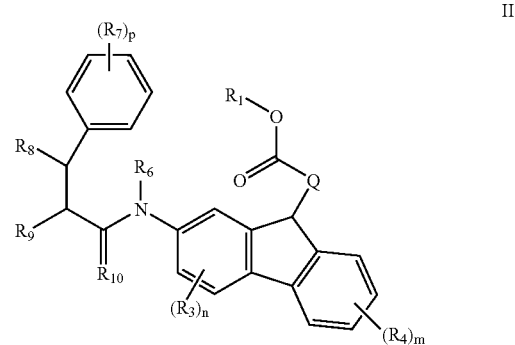

wherein

Q is alkyl, alkenyl or alkynyl optionally substituted with halogen, carboxyl, alkyl or aryl, and wherein one or more carbon atoms are optionally replaced with O, N, NR₆, S, SO, or SO₂;

R₁ is hydrogen or is selected from the group consisting of alkyl, alkenyl and alkynyl, each of which is optionally substituted with hydroxyl, halogen, amino, nitro, carboxyl, a carbocycle, or a heterocycle; or R₁ is a carbocycle or heterocycle optionally substituted with hydroxyl, oxo, halogen, amino, or nitro;

R₃ and R₄ are independently selected from the group consisting of H, hydroxyl, halogen, amino, nitro, carboxyl, alkyl, alkenyl, alkynyl, a carbocycle and a heterocycle, wherein said alkyl, alkenyl, alkynyl, carbocycle and heterocycle groups are optionally substituted with one or more substituents selected from the group consisting of hydroxyl, halogen, amino, oxo and carboxyl, and optionally one or more carbon atoms of said alkyl, alkenyl and alkynyl group is replaced with N, NR₆, O, S, SO or SO₂;

R₆ is hydrogen, alkyl, alkenyl or alkynyl;

R₇ is hydrogen, hydroxyl, halogen, alkyl, alkoxy or halogen substituted alkyl;

R₈ is H, alkyl, alkenyl or alkynyl;

R₉ is H or NR₁₁R₁₁', wherein R₁₁ and R₁₁' are independently H, acyl or and amino acid residue; or one of R₁₁ and R₁₁' together with R₈ form a heterocycle;

R₁₀ is O or S;

m and n are independently 1, 2 or 3;

p is an integer from 1 to 5;

and salts, solvates and hydrates thereof.

In a preferred embodiment $R_7$ is hydroxyl at the para-position (i.e. 4-position) of the phenyl group. Further $R_7$ substituents as provided when 'p' is the integer 2, 3, 4 or 5, include 3-iodo, 3-fluoro, 3-chloro and 2,3,5,6-tetrafluoro.

In particular embodiments, $R_6$ and $R_8$ are H and $R_{10}$ is oxygen. Alternatively, $R_6$ is methyl.

In a preferred embodiment, $R_9$ is $NR_{11}R_{11'}$ wherein $R_{11}$ is H and $R_{11'}$ is H or acyl, in particular alkanoyl i.e. acetyl. In another preferred embodiment, $R_9$ is $NR_{11}R_{11'}$ wherein one of $R_{11}$ and $R_{11'}$ together with $R_8$ form a 5-member heterocycle while the other of $R_{11}$ and $R_{11'}$ is H or $C_{1-4}$ alkanoyl. Preferably $R_{11}$ and $R_8$ together form a pyrrolidine ring and $R_{11'}$ is H or alkanoyl i.e. acetyl.

Particular compounds of the invention include:

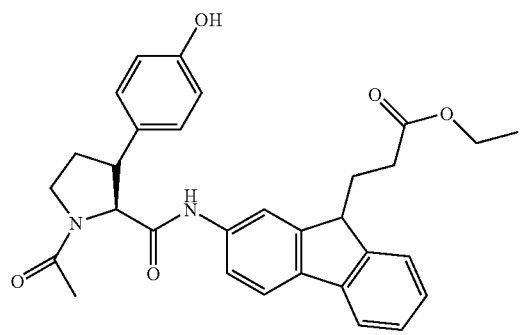

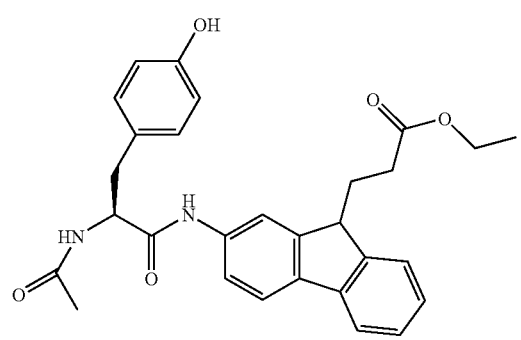

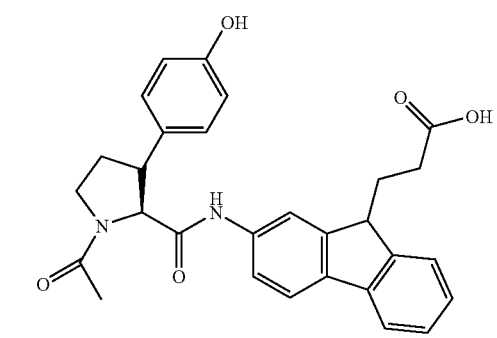

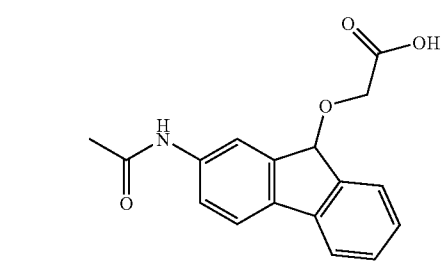

-continued

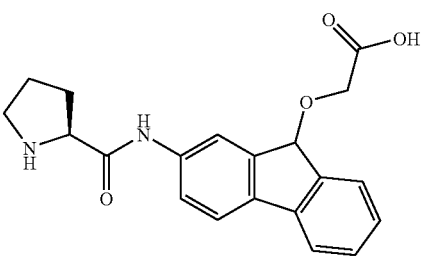

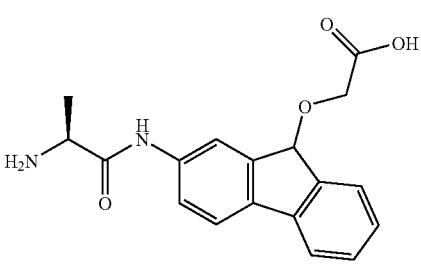

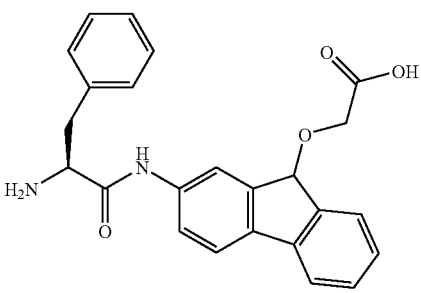

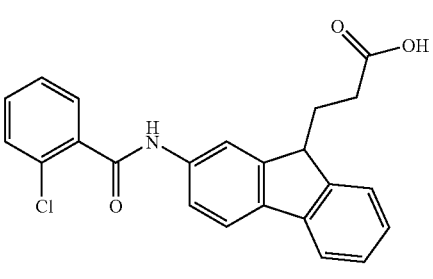

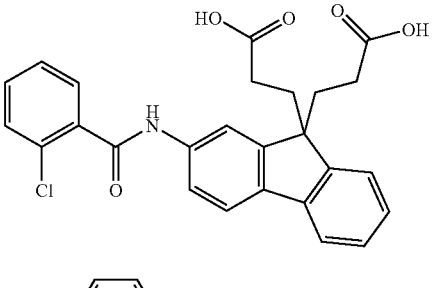

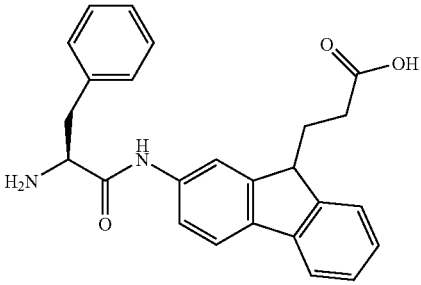

-continued
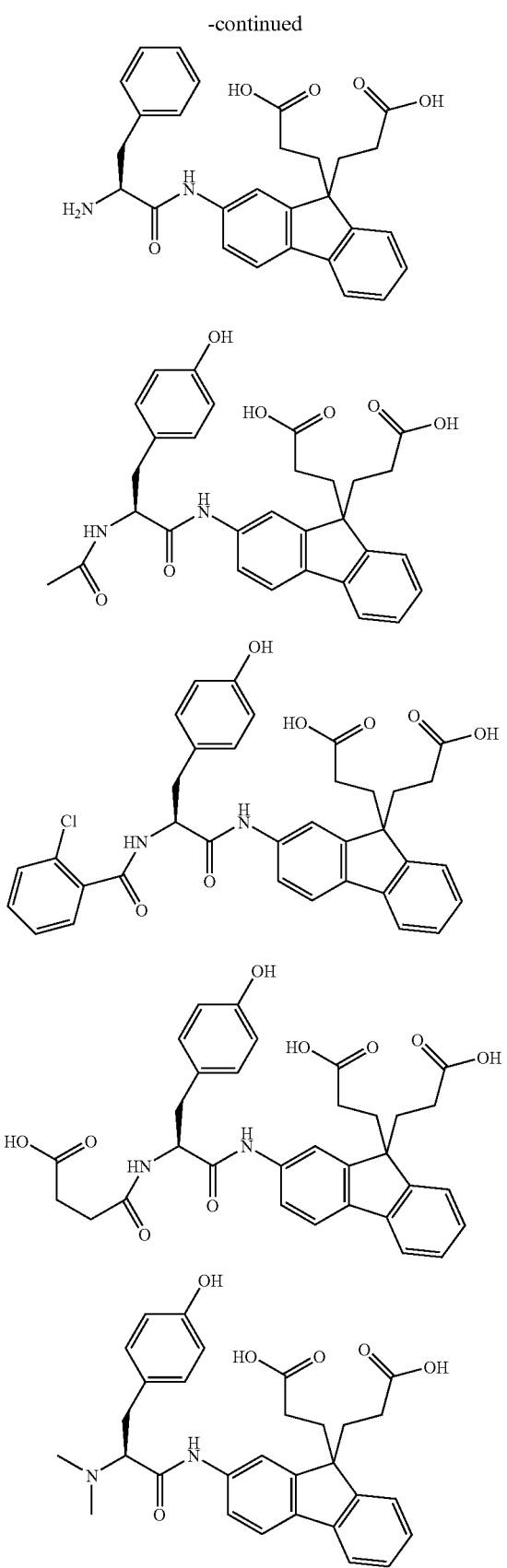
-continued
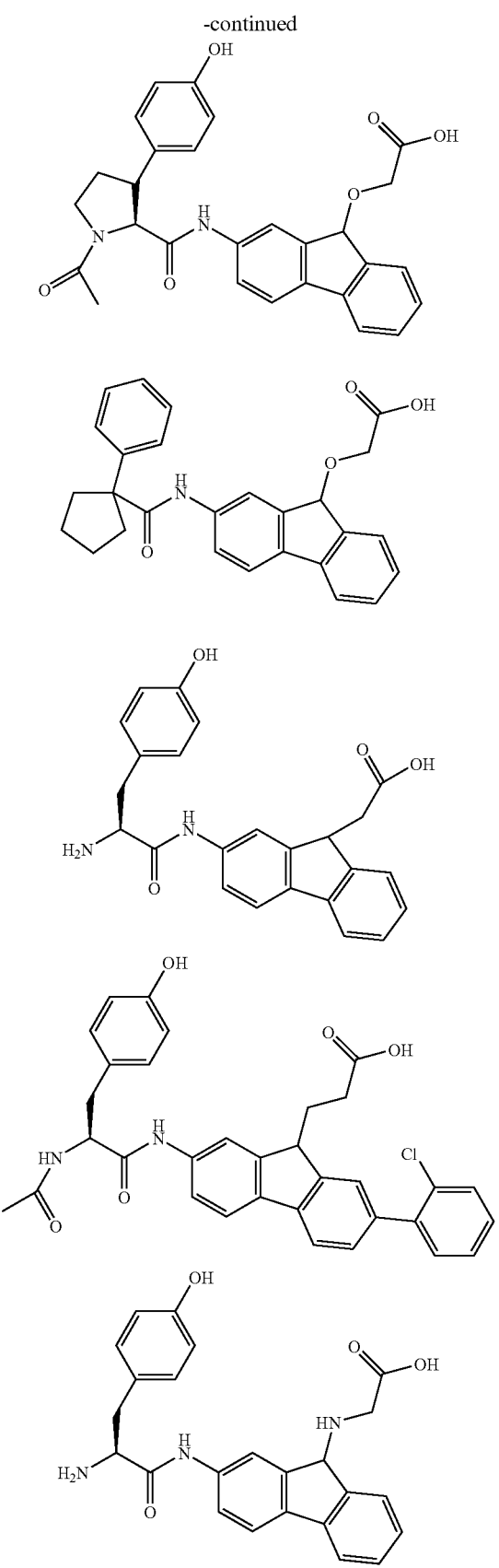

-continued
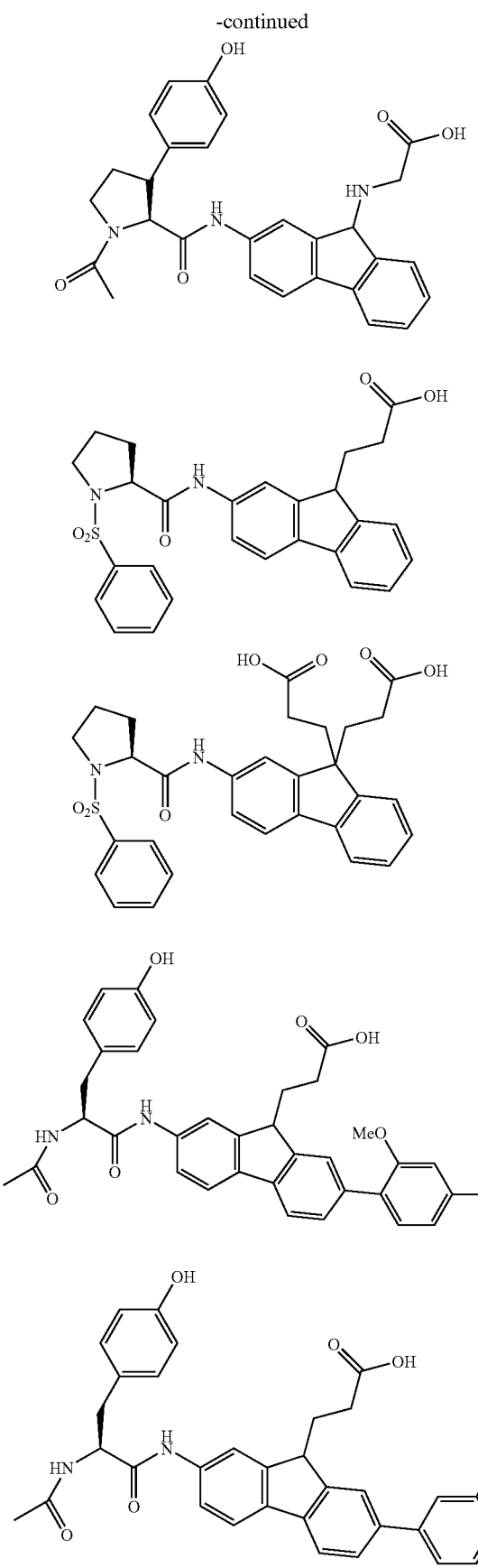
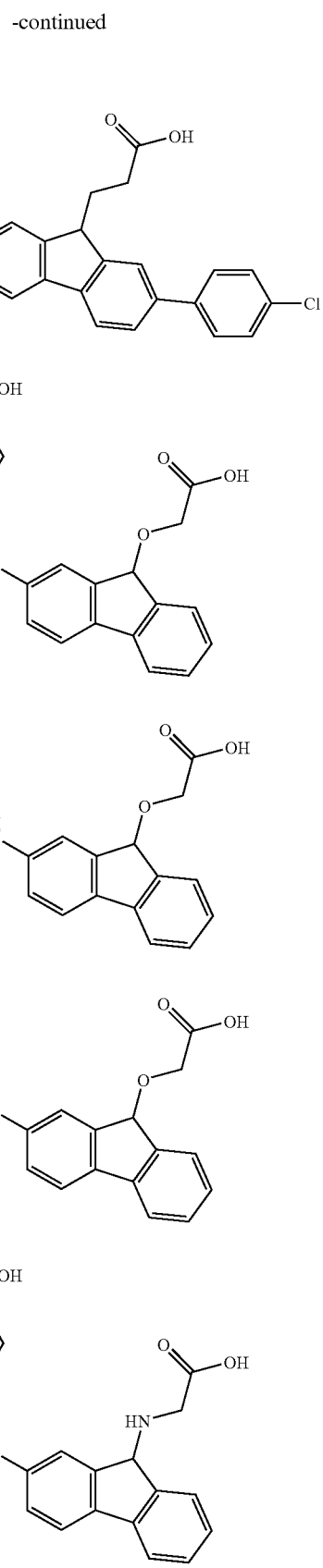

-continued
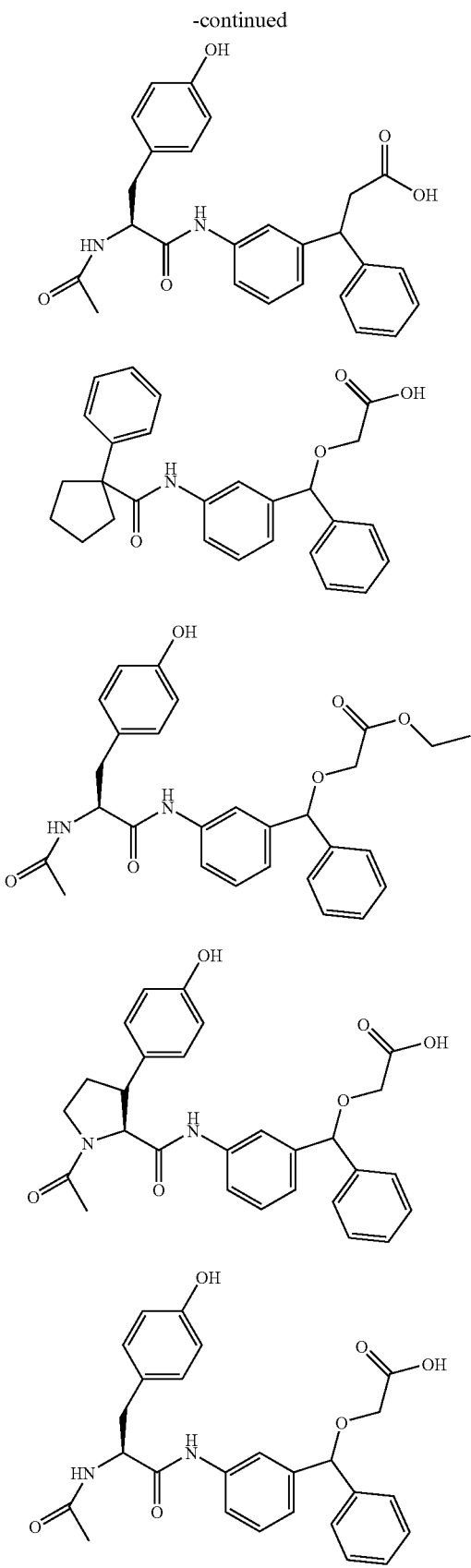
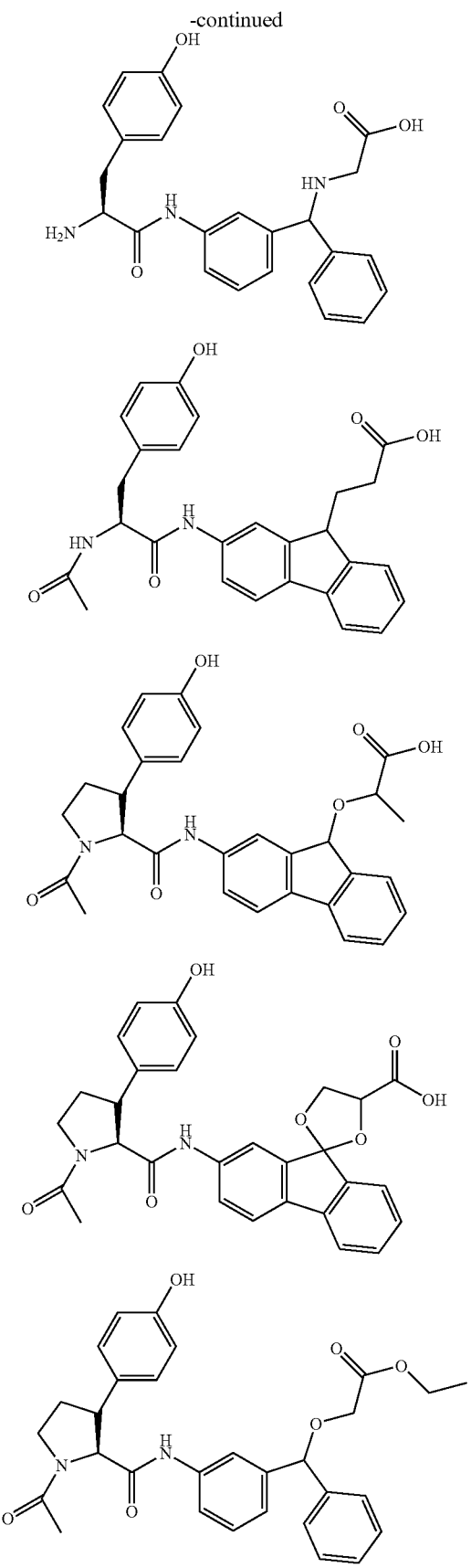

-continued

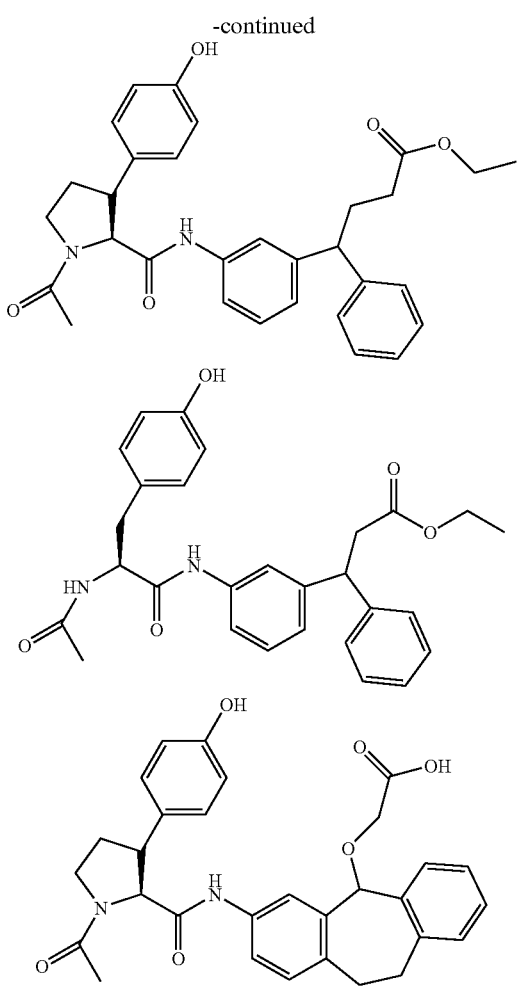

and salts, solvates and hydrates thereof.

It will be appreciated that compounds of the invention may incorporate chiral centers and therefore exist as geometric and stereoisomers. All such isomers are contemplated and are within the scope of the invention whether in pure isomeric form or in mixtures of such isomers as well as racemates. Stereoisomeric compounds may be separated by established techniques in the art such as chromatography, i.e. chiral HPLC, or crystallization methods.

"Pharmaceutically acceptable" salts include both acid and base addition salts. Pharmaceutically acceptable acid addition salt refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

Pharmaceutically acceptable base addition salts include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

Compounds of the invention may be prepared according to established organic synthesis techniques from starting materials and reagents that are commercially available. In general, the compounds may be prepared starting from a commercially available central ring system. Depending on the particular compound to be prepared, the central ring system is manipulated to append first the carboxylate moiety —Q—C(O)O—$R_1$ to X and then the $R_2$—W— moiety to the benzene ring, or alternatively first appending the $R_2$—W— moiety and then the —Q—C(O)O—$R_1$ moiety.

In a particular embodiment, compounds of formula (Ia), wherein X is C and Q incorporates an oxygen adjacent to X (i.e. an ether), are prepared according to the general scheme 1.

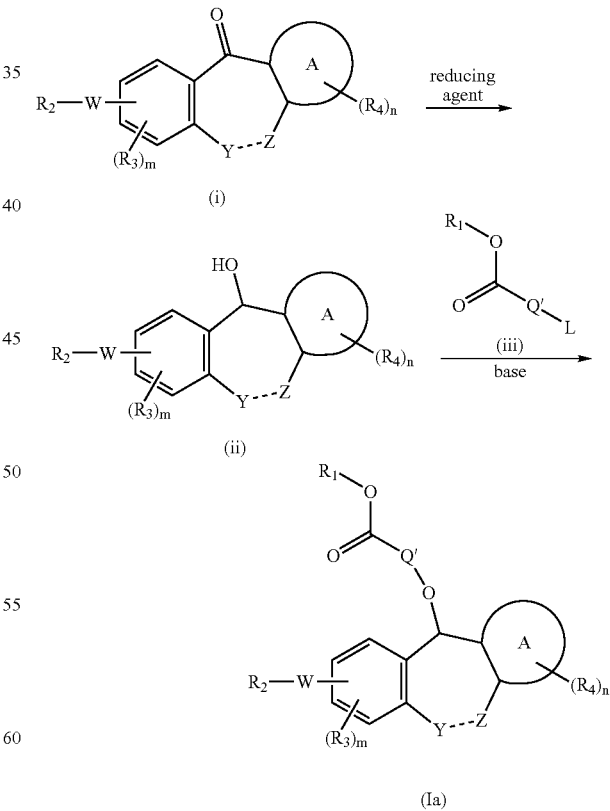

Referring to scheme 1, starting compound (i), wherein A, Y, Z, W, $R_2$-$R_4$, m and n are as previously defined, is reduced with a suitable reducing agent, such as sodium borohydride (NaBH$_4$) or equivalent hydride, to give alcohol (ii). Depending on the particular substituents, starting compound (i) may be commercially available or is otherwise prepared according to established organic synthetic techniques from compounds that are commercially available. The final ether compound (Ia) of the invention is achieved by treating alcohol (ii) with an base such as NaH followed by reacting with elecrophilic intermediate (iii), wherein L is a suitable leaving group such as a halogen i.e. Br, and Q' is the same as Q, i.e. a carboxyl substituted alkyl, alkenyl or alkynyl chain, minus the first carbon atom that would be adjacent to the ring system. It will be appreciated that depending on the particular substituents present in the compound, suitable protection and deprotection procedures will be required as is standard in the art. Numerous protecting groups are described in Greene and Wuts, Protective Groups in Organic Chemistry, 2d edition, John Wiley and Sons, 1991, as well as detailed protection and deprotection procedures. For example, suitable amino protecting groups include t-butyloxycarbonyl (Boc), fluorenyl-methyloxycarbonyl (Fmoc), 2-trimethylsilyl-ethyoxycarbonyl (Teoc), 1-methyl-1-(4-biphenylyl)ethoxycarbonyl (Bpoc), allyloxycarbonyl (Alloc), and benzyloxycarbonyl (Cbz). Carboxyl groups can be protected as fluorenylmethyl groups and hydroxyl groups may be protected with trityl, monomethoxytrityl, dimethoxytrityl, and trimethoxytrityl groups.

Preparation of compounds of the invention wherein X is carbon and Q is an alkyl chain, may be accomplished according to scheme 2.

Referring to scheme 2, starting compound (i) is reacted with a non-nucleophilic base such as NaH, LDA or TBAF, to give carbanion (ii) which is subsequently reacted with intermediate (iii) to yield compound of formula (Ib) of the invention. In a particular embodiment wherein Q is and optionally substituted $C_2$ alkyl linker to —$COOR_1$, intermediate carbanion (ii) is reacted with an α, β unsaturated carboxylate (iv) wherein each R is independently hydrogen, halogen, alkyl, carboxyl or aryl, to give compound (Ib) of the invention. Preferably R is halogen or $C_{1-4}$ alkyl i.e. methyl.

In another embodiment, compounds of formula (I), wherein X is N, are prepared according to scheme 3.

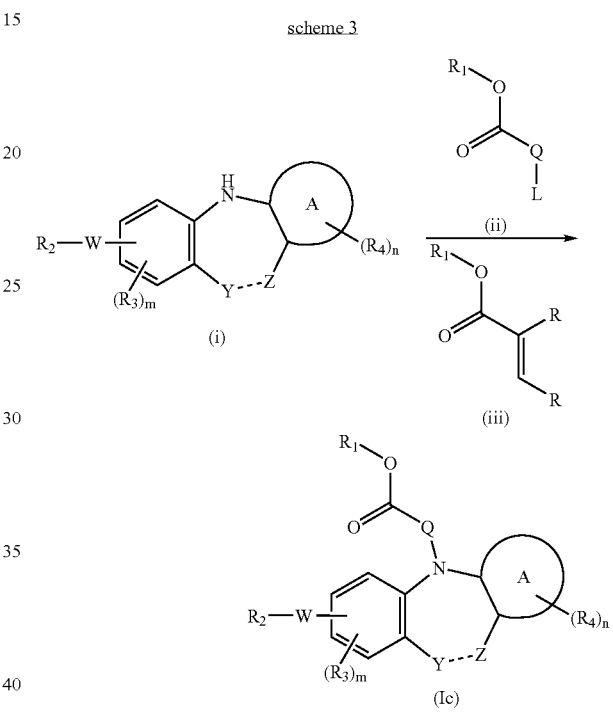

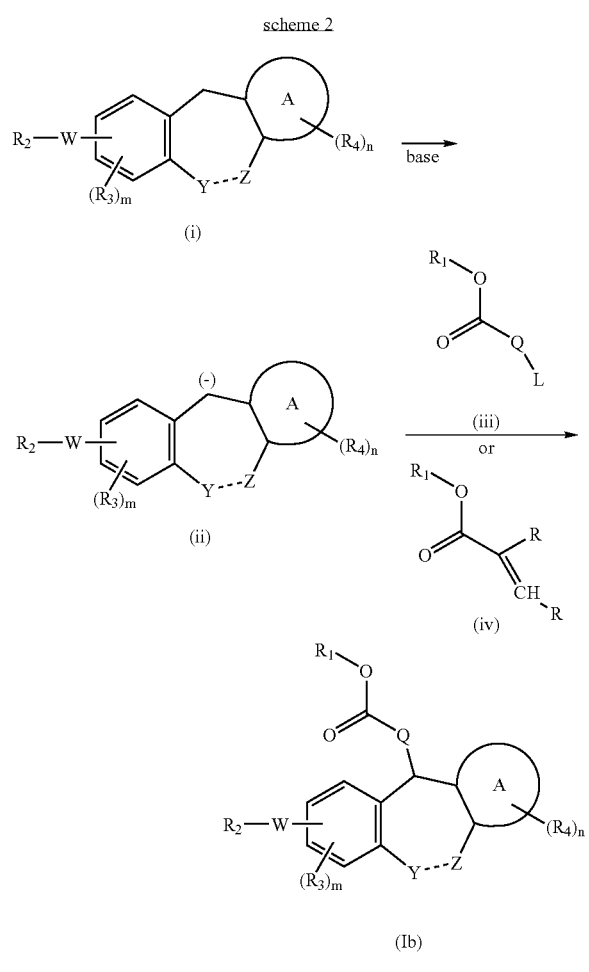

Referring to scheme 3, starting compound (i) is reacted with intermediate (ii) wherein L is a suitable leaving group, i.e. Br, in the presence of a non-nucleophilic base such as $Cs_2CO_3$ or $KCO_3$ to yield the final compound (Ic) of the invention. Alternatively, starting compound (i) can be reacted with an α, β unsaturated carboxylate (iii) as in scheme 2 to give compound (Ic) of the invention.

In another embodiment, compounds of formula (I) wherein W is —C(O)NH—, —$SO_2$NH— or —NH— are prepared according to scheme 4.

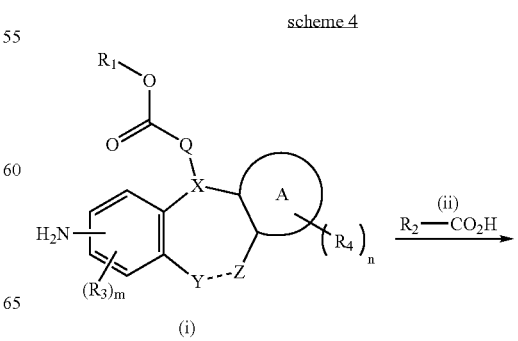

-continued

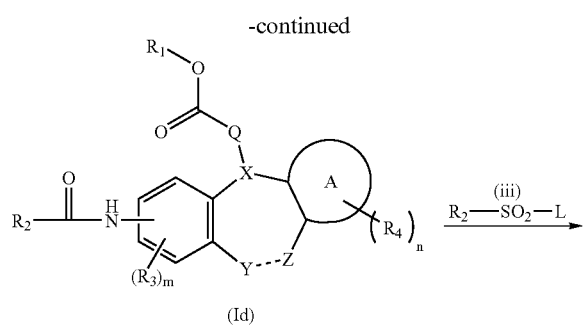

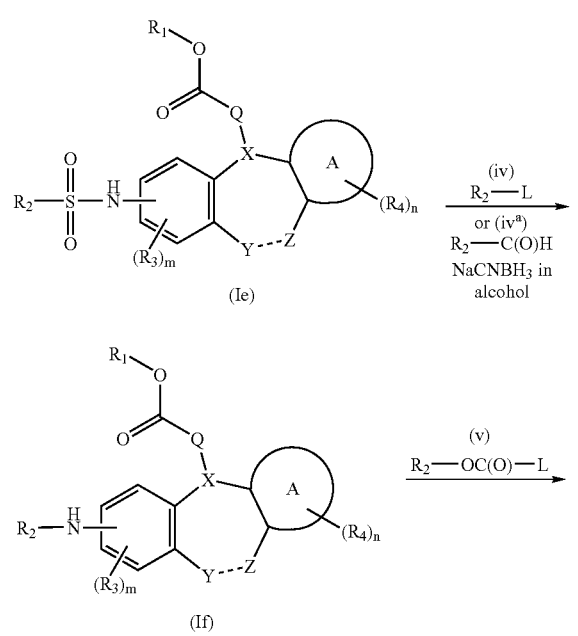

Referring to scheme 4, from the starting amine compound (i) may be prepared amide (Id), sulfonamide (Ie), amine (If), carbamate (Ig) and urea (Ih) by reacting (i) respectively with intermediates (ii) an activated ester of $R_2$—$CO_2H$, (iii) $R_2$—$SO_2$-L wherein L is a leaving group such as a halogen, (iv) $R_2$-L in the presence of a non-nucleophilic base or $R_2$—C(O)H in the presence of $NaCNBH_3$, (v) $R_2$—OC(O)-L, and (vi) isocyanate $R_2$—N=C=O. It will be appreciated that thioamides may be prepared in a similar manner as the amides by using $R_2$—C(S)H or $R_2$—C(S)O—; and thiocarbamates may be prepared using $R_2$—S—C(O)-L or $R_2$—OC(S)-L; and thioureas may be prepared using isothiocyanate $R_2$—N=C=S. In a particular In another embodiment, compounds of formula (I) wherein W is —O— or —S— may be prepared according to scheme 5a and 5b.

scheme 5a

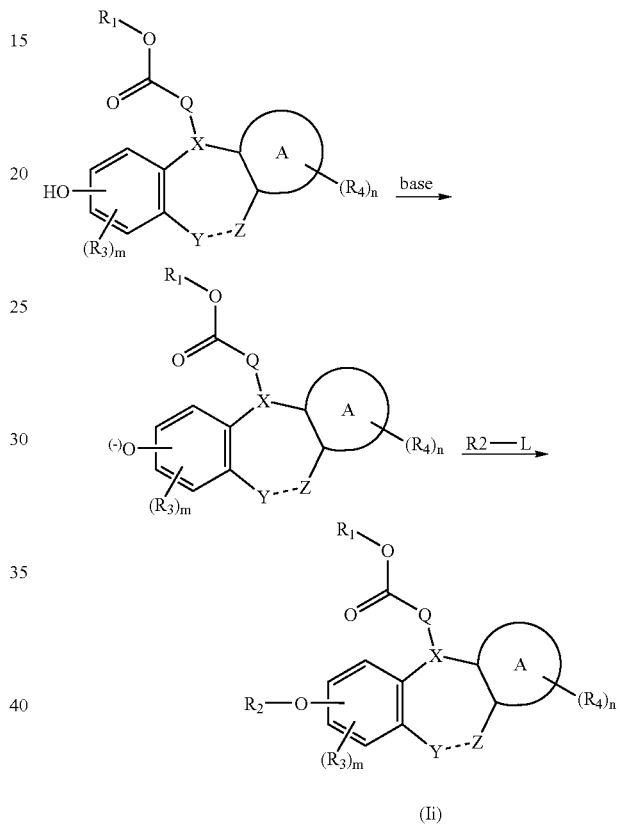

scheme 5b

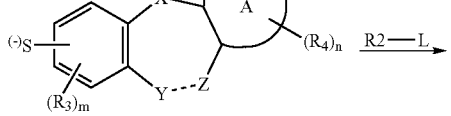

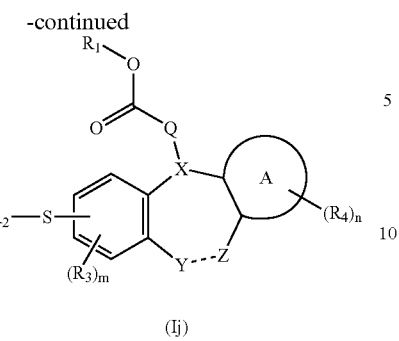

(Ij)

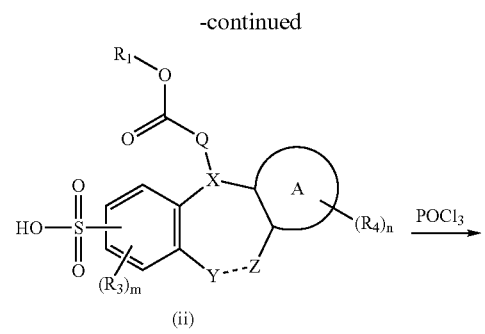

(ii)

Referring to schemes 5a and 5b, the starting hydroxyl or thiol compound is reacted with a non-nucleophilic base such as NaH to remove a proton. The anion is then reacted with $R_2$-L wherein L is a suitable leaving group to yield the resulting ether (Ii) and thioether (Ij) compound of the invention.

In another embodiment compounds of formula (I), wherein W is carbonyl —C(O)—, may be prepared according to scheme 6.

scheme 6

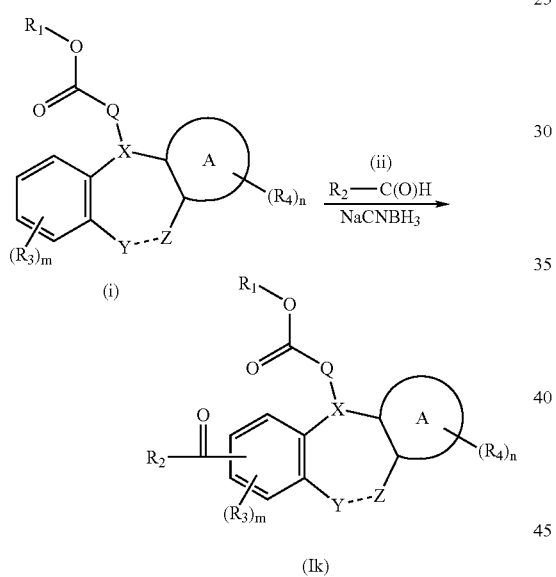

(Ik)

Referring to scheme 6, starting compound (i) is reacted with aldehyde intermediate (ii) in the presence of NaCNBH₃ to give compound (Ik) of the invention.

In another embodiment, compounds of formula (I), wherein W is —NR₆SO₂—, are prepared according to scheme 7.

scheme 7

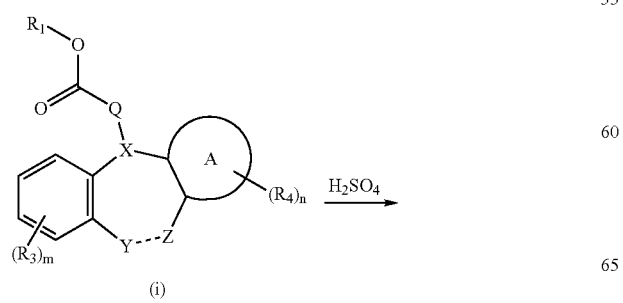

(iii)

(Il)

Referring to scheme 7, starting compound (i) is reacted with sulfuric acid and then POCl₃ to give the sulfonyl chloride compound (iii) which is reacted with $R_2$—NH₂ to give compound (Il) of the invention.

In another embodiment, compounds of formula (I), wherein W is C, may be prepared according to scheme 8.

scheme 8

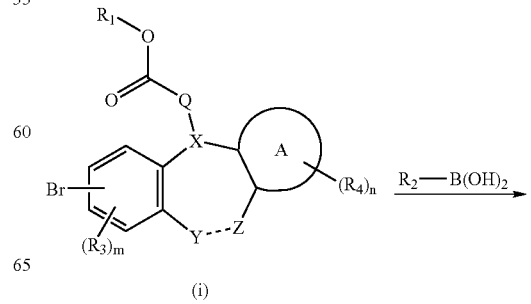

(i)

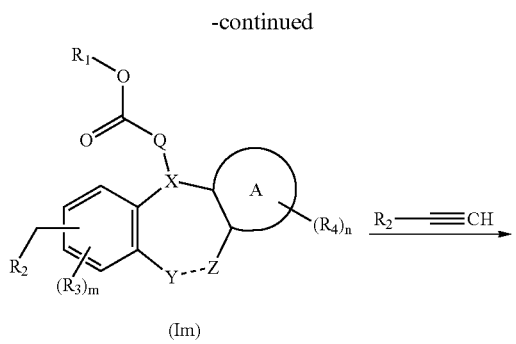

(Im)

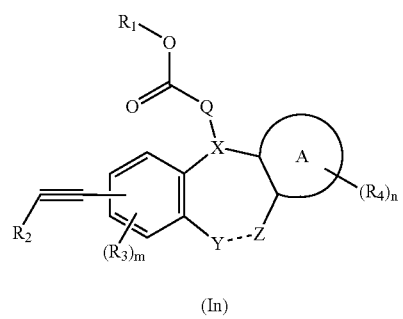

(In)

Referring to scheme 8, starting compound (i) is reacted with Pd° catalyst followed by $R_2$—$B(OH)_2$ or $R_2$—C≡CH to give final compound (Im) or (In) respectively.

In another embodiment, compounds of formula (I), wherein W is carbamate —$NR_6C(O)O$— or thiocarbamate —$NR_6C(S)O$—, may be prepared according to scheme 9.

scheme 9

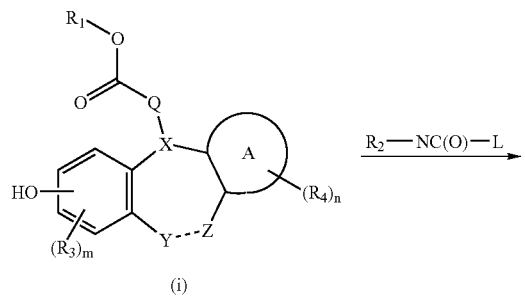

(i)

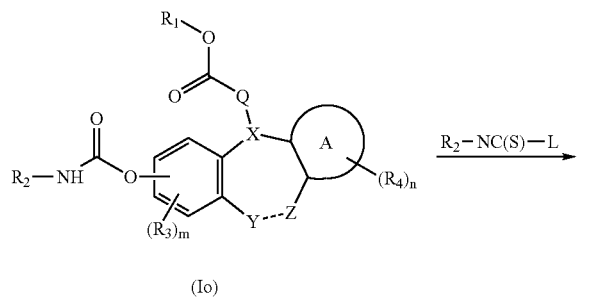

(Io)

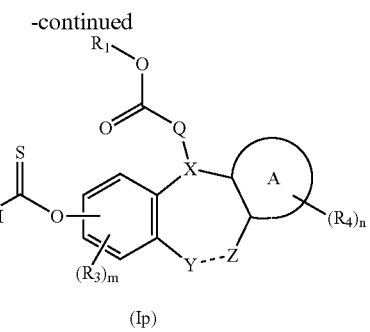

(Ip)

Referring to scheme 9, starting alcohol compound is reacted with intermediate $R_2$—NC(O)-L or $R_2$—NC(S)-L, wherein L is a suitable leaving group such as Br, to give final compound of the invention (Io) or (Ip) respectively. In a particular embodiment, a morpholino carbamate compound of the invention by reacting the starting alcohol with morpholine-C(O)—Cl.

In another embodiment, compounds of formula (I), wherein W is thiocarbamate —$NR_6C(O)S$— or thiocarbamate —$NR_6C(S)S$—, may be prepared according to scheme 10.

scheme 10

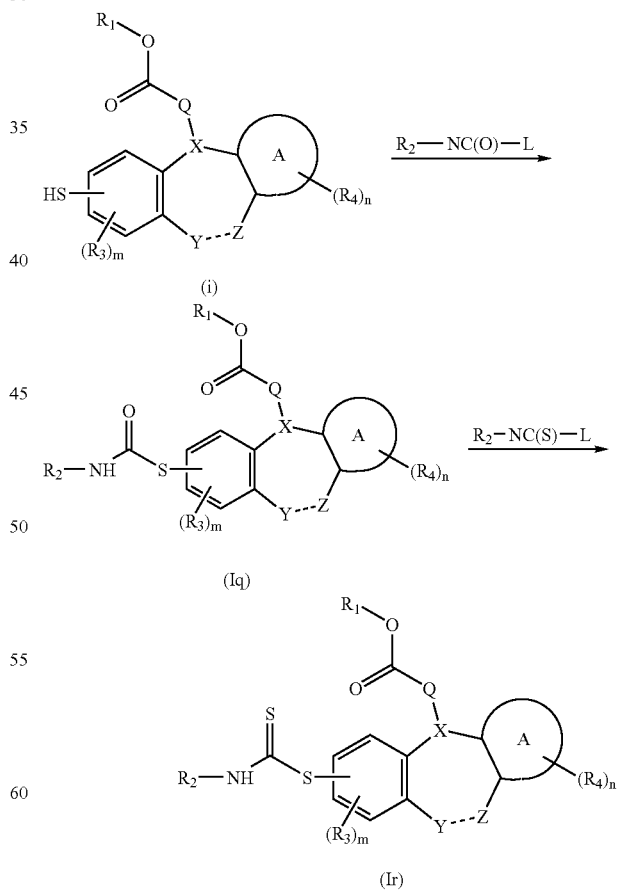

Referring to scheme 10, starting thiol compound (i) is reacted with intermediate $R_2$—NC(O)-L or $R_2$—NC(S)-L, wherein L is a suitable leaving group such as Br, to give final compound of the invention (Iq) or (Ir) respectively.

In an aspect of the invention, there is provided a method of inhibiting binding of an $\alpha_4$ integrin to a ligand, the method comprising contacting said $\alpha_4$ integrin with a compound of formula (I). The method may be carried out as a solution based or cell based assay wherein the compound of the invention is introduced to the integrin in the presence of a putative or known ligand of the integrin. The compound may be labeled, for example isotopically radiolabeled, to facilitate detection of ligand binding or lack thereof to the integrin. Thus compounds of the invention are useful for diagnostic assays.

Compounds of the invention are useful to prevent the interaction of an epithelial cell bearing VCAM-1 and/or MAdCAM on the cell surface with a leukocyte cell bearing $\alpha_4\beta_1$ and/or $\alpha_4\beta_7$ on the surface by contacting the epithelial cell or the leukocyte with an inhibitory amount of the compound of the invention. The compounds are useful in assays to determine the inhibitory effect of a compound which antagonizes the binding of $\alpha_4\beta_1$ and/or $\alpha_4\beta_7$ integrin to VCAM-1 ligand and/or MAdCAM ligand. The inhibitory compound may be a small molecule, a protein or peptide or an antibody. In an in vitro assay, the ligand or the integrin may be directly or indirectly bound to a surface, such as microtiter plate, using known methods described for example in WO 9820110, WO 9413312, WO 9624673, WO 9806248, WO 9936393, and WO 9910312. The other member of the binding pair, e.g. the integrin or the ligand, respectively, (or a cell expressing the same on its surface) is then added to the surface bound member and the inhibitory effect of a test molecule is determined. The inhibitory activity of the compounds of the invention can also be determined with this type of assay.

The binding of the integrins to their respective ligands is known to be involved in inflammatory conditions associated with leukocyte infiltration of tissues lined with epithelial cells expressing VCAM-1 or MAdCAM. Such tissues include the gastrointestinal tract, skin, urinary tract, respiratory airways and joint synovial tissues. The compounds of the invention are useful in treating diseases in which such binding is implicated as a cause of the disease or symptoms of the disease. Undesired disease symptoms may arise from cell adhesion and/or cell activation which releases proinflammatory mediators, typically when there is an increase or upregulation in the expression of VCAM-1 and/or MAdCAM on the surface of endothelial cells. Various disease states which can be treated and for which the inflammatory symptoms can be reduced upon administration of the compounds of the invention include rheumatoid arthritis, asthma, psoriasis, multiple sclerosis, inflammatory bowel disease including ulcerative colitis, pouchitis and Crohn's disease, Celiac disease, nontropical Sprue, graft-versus-host disease, pancreatitis, insulin-dependent diabetes mellitus, mastitis, cholecystitis, pericholangitis, chronic sinusitis, chronic bronchitis, pneumonitis, collagen disease, eczema, and systemic lupus erythematosus. Compounds of the invention are useful in treating these diseases and conditions by inhibiting the integrin/ligand binding.

Compounds of the invention are therapeutically and/or prophylactically useful for treating diseases or conditions mediated by $\alpha_4$ integrin receptors i.e. $\alpha_4\beta_1$ and $\alpha_4\beta_7$, and/or their ligands, in particular VCAM-1 and MADCAM-1. Accordingly in an aspect of the invention, there is provided a method of treating a disease or condition mediated by the $\alpha_4$ integrin receptors or ligands of $\alpha_4$ integrin receptor ligands in a mammal, for example a human, comprising administering to said mammal an effective amount of a compound of the invention. By "effective amount" is meant an amount of compound which upon administration is capable of reducing the amount of ligand able to bind to $\alpha_4$ integrins in vivo; or an amount of compound which upon administration is capable of alleviating or reducing the severity of symptoms associated with the disease or condition mediated by $\alpha_4$ integrins or ligands thereof.

The actual amount of compound administered and the route of administration will depend upon the particular disease or condition as well as other factors such as the size, age, sex and ethnic origin of the individual being treated and is determined by routine analysis. In methods of the invention, the compound may be administered orally (including buccal, sublingual, inhalation), nasally, rectally, vaginally, intravenously, intradermally, subcutaneously and topically. Compounds will be formulated into compositions suitable for administration for example with suitable carriers, diluents, thickeners, adjuvants etc. as are routine in the formulation art. Accordingly, another aspect of the invention provides pharmaceutical compositions comprising a compound of formula (I) and a pharmaceutically acceptable carrier, excipient or adjuvant.

Compositions of the invention may also include additional active ingredients. Dosage forms include solutions, powders, tablets, capsules, gel capsules, suppositories, topical ointments and creams and aerosols for inhalation. Formulations for non-parenteral administration may include sterile aqueous solutions which may also contain buffers, diluents and other suitable additives. Pharmaceutically acceptable organic or inorganic carrier substances suitable for non-parenteral administration which do not deleteriously react with compounds of the invention can be used. Suitable pharmaceutically acceptable carriers include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like. The formulations can be sterilized and, if desired, mixed with auxiliary agents, e.g., lubricants, preservatives, stabilizers, wetting agents, emulsifiers, salts for influencing osmotic pressure, buffers, colorings flavorings and/or aromatic substances and the like which do not deleteriously react with compounds of the invention. Aqueous suspensions may contain substances which increase the viscosity of the suspension including, for example, sodium carboxymethylcellulose, sorbitol and/or dextran. Optionally, the suspension may also contain stabilizers.

In a preferred embodiment, compounds of the invention are administered via oral delivery. Compositions for oral administration include powders or granules, suspensions or solutions in water or non-aqueous media, capsules, sachets, troches, tablets or SECs (soft elastic capsules or caplets). Thickeners, flavoring agents, diluents, emulsifiers, dispersing aids, carrier substances or binders may be desirably added to such formulations Such formulations may be used to effect delivering the compounds to the alimentary canal for exposure to the mucosa thereof. Accordingly, the formulation can consist of material effective in protecting the compound from pH extremes of the stomach, or in releasing the compound over time, to optimize the delivery thereof to a particular mucosal site. Enteric coatings for acid-resistant tablets, capsules and caplets are known in the art and typically include acetate phthalate, propylene glycol and sorbitan monoleate.

Various methods for producing formulations for alimentary delivery are well known in the art. See, generally *Remington's Pharmaceutical Sciences*, 18th Ed., Gennaro, ed., Mack Publishing Co., Easton, Pa., 1990. The formulations of the invention can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound should in each case be present in a concentration of about 0.5% to about 99% by weight of the total mixture, that is to say in amounts which are sufficient to achieve the desired dosage range. The formulations are prepared, for example, by extending the active compounds with solvents and/or excipients, if appropriate using emulsifying agents and/or dispersing agents, and, for example, in the case where water is used as the diluent, organic solvents can be used as auxiliary solvents if appropriate.

Compositions may also be formulated with binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrates (e.g., starch or sodium starch glycolate); or wetting agents (e.g., sodium lauryl sulfate). Tablets may be coated by methods well known in the art. The preparations may also contain flavoring, coloring and/or sweetening agents as appropriate.

Formulations of the present invention suitable for oral administration may be presented as discrete units such as capsules, cachets or tablets each containing predetermined amounts of the active ingredients; as powders or granules; as solutions or suspensions in an aqueous liquid or a non-aqueous liquid; or as oil-in-water emulsions or water-in-oil liquid emulsions. A tablet may be made by compression or molding, optionally with one or more accessory ingredients. Compressed tablets may be prepared by compressing in a suitable machine, the active ingredients in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredients therein.

EXAMPLE 1

Synthesis of Compound 5

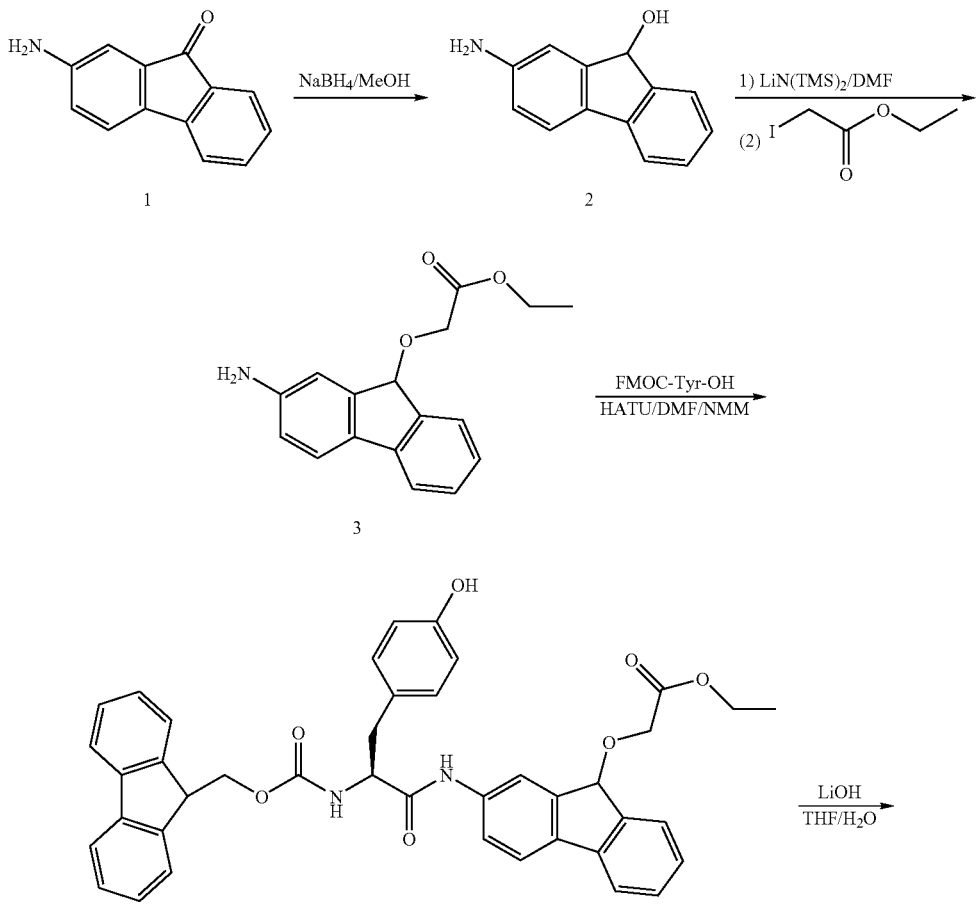

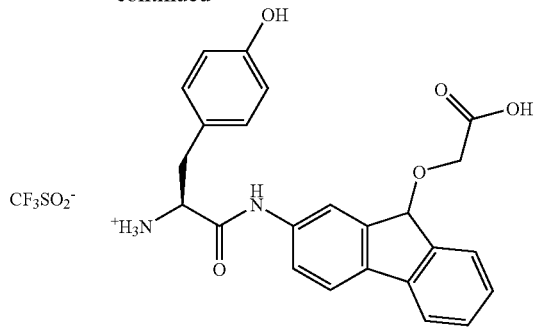

Commercially available 2-amino-9-fluorenone 1 (10 mmol) was dissolved in 100 mL of methanol and 0.38 g (10 mmol) of sodium borohydride was added. The mixture was stirred at 25° C. for 1 h and concentrated to dryness under vacuum. The residue was suspended in 100 mL of saturated aqueous $NaHCO_3^-$ and extracted with ethylacetate (100 mL). The ethylacetate layer was concentrated under vacuum and the residue was crystallized from ethylacetate/hexane (2:1) to afford 1.4 g of pure 2-amino-9-hydroxyfluorene 2.

Compound 2 (0.39 g; 2 mmol) was dissolved in 50 mL of anhydrous DMF and cooled to 0° C. under nitrogen. Lithium bistrimethylsilylamide (2 mmol; 1M in THF) was added dropwise and stirring was continued for 30 min. Iodoethylacetate (3 mmol) was added dropwise and the solution was stirred 12 h at $_0$° C. The reaction mixture was poured into 200 mL of water and extracted with ethyl acetate (200 mL). The extract was concentrated and the product was purified via silica gel chromatography (25% ethylacetate/hexane) to afford 0.34 g of fluorenyl ether 3.

Fluorenyl ether 3 (0.28 g; 1 mmol) was dissolved in 5 mL of DMF and N-FMOC L-tyrosine (1 mmol) was added followed by HATU (1 mmol) and N-methylmorpholine (2 mmol). The reaction was stirred overnight at 25° C., poured into 50 mL water, and the product extracted with ethylacetate. Concentration under vacuum afforded 0.5 g of crude 4 which was used directly in the next step without further purification.

Compound 4 (0.5 g) was dissolved in 1:1 THF/water and 3 mL LiOH (1M in water) was added. The reaction was stirred for 4 h at 25° C. and concentrated under vacuum to remove most of the THF. The aqueous solution was lyophilized and the crude product was purified by reverse HPLC (acetonitrile/water gradient) to afford 90 mg of pure 5 as the TFA salt.

EXAMPLE 2

Synthesis of 2-amino Carbazole

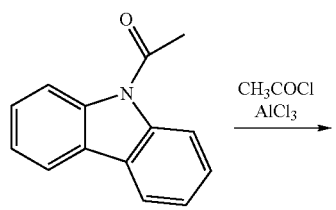

Carbazole (100.24 g) was suspended in acetic anhydride (300 mL) with catalytic boron trifluoride etherate (0.65 mL) and the solution refluxed for 25 min. then cooled to 0° C. and the solid was then collected and recrystallized from hexane to give 82.65 g 9-acetyl-carbazole.

9-Acetyl-carbazole (41.85 g, 0.2 mol) was dissolved in 1 L methylene chloride and 28.5 mL acetylchloride (0.4 mol) and 120 g aluminum chloride (0.9 mol) were added and the solution refluxed for 1.5 h. The solution was cooled to −78° C. and 6N HCl was added slowly while stirring and allowed to warm to room temperature. Methylene chloride was added to dissolve the precipitate and the solution was extracted, and the organics dried over $Na_2SO_4$, decolorized with charcoal, filtered and concentrated. Recrystallization from benzene/hexane gave 27.9 g 2,9-diacetylcarbazole.

2,9-Diacetylcarbazole, (25.1 g, 0.1 mol) was dissolved in 100 mL pyridine. Hydroxylamine hydrochloride (10.42 g, 0.15 mol) was added and the solution refluxed for 20 min. The mixture was cooled and poured into 70 mL conc. HCl in ice. The precipitate was collected by filtration, washed with a large volume of water and dried in vacuum over KOH to yield 24 g white solid. 5 g of this solid (18.8 mmol) was dissolved in 17 mL TFA and 0.3 mL trifluoroacetic anhydride (2.1 mmol) was added. The mixture was refluxed for 20 min then concentrated to give the crude 2,9-diacetylcarbazole amine. Both acetyl groups were removed by suspending the crude material in 400 mL 10% aq. KOH and refluxing for 1 day. The solution was cooled and ethyl acetate added and the product 2-aminocarbazole was extracted, washed with brine, dried over $Na_2SO_4$ and concentrated.

EXAMPLE 3

Synthesis of Compound 6

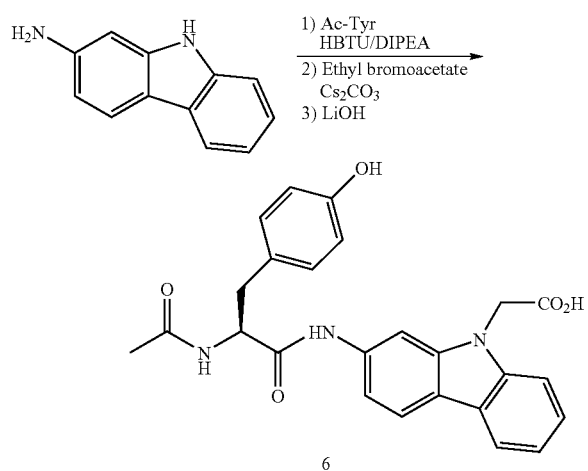

6

To 0.1 g (0.55 mmol) 2-aminocarbazole in 6 mL DMF was added 0.37 g (1.65 mmol) of N—Ac-L-Tyr, 0.37 g (1.65 mmol) HBTU and 0.3 mL (1.7 mmol) DIPEA. The reaction was stirred for 1 h, poured into ethyl acetate and washed consecutively with 0.1N $H_2SO_4$, aq. $NaHCO_3$ and brine then dried over $Na_2SO_4$ and concentrated. Flash chromatography (10% methanol/methylene chloride) gave 0.16 g (0.26 mmol) of the acetylated amine. This was stirred for 1 h with cesium carbonate (0.185 g, 0.57 mmol) and ethyl bromoacetate (0.043 mL, 0.39 mmol) in 4 mL DMF and then poured into ethyl acetate and washed with saturated $NH_4Cl$ and brine and dried over $Na_2SO_4$ and concentrated. Without purification this was dissolved in 5 mL THF and 5 mL water and 0.043 g (1 mmol) LiOH was added. The ester was cleaved in <30 min and then diluted with ethyl acetate and washed consecutively with 0.1N $H_2SO_4$, and brine and then dried over $Na_2SO_4$ and concentrated. The product was lyophilized and purified by HPLC.

EXAMPLE 4

Synthesis of Compound 7

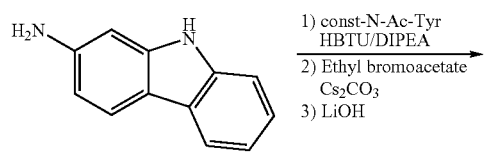

-continued

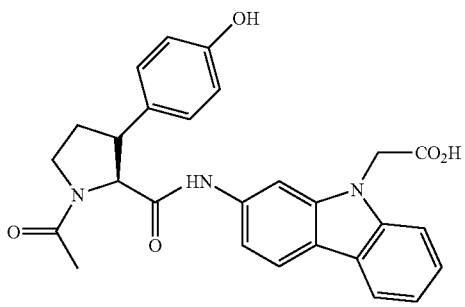

7

To 6.57 g (31.44 mmol) of the 9-acetylcarbazole in 200 mL $CH_2Cl_2$ was added 10.68 g silver nitrate (63 mmol) and 25.1 g aluminum chloride (188.6 mmol). This was stirred at room temperature for 2 h, diluted with methylene chloride and poured onto ice containing 82 mL conc. HCl. The organic layer was separated, washed three times with water, dried with $MgSO_4$ and concentrated to a dark brown solid. The solid was dissolved in 200 mL methanol, 4% aq KOH was added and the solution was refluxed for 1 h. The solution was cooled and concentrated, then taken up in ethyl acetate and washed consecutively with water and brine then dried over $Na_2SO_4$. The 9-nitrocarbazole (0.1 g, 0.47 mmol) was dissolved in 3 mL DMF and 0.13 mL (1.42 mmol) methyl acrylate and 0.69 g (2.12 mmol) $Cs_2CO_3$ were added. The reaction was stirred for 2 h, diluted with ethyl acetate and washed with saturated $NH_4Cl$ and brine and then dried over $Na_2SO_4$ and concentrated. Flash chromatography (25% ethyl acetate/hexane) gave 0.081 g alkylated 9-nitrocarbazole. This was dissolved in 5 mL methanol and a spatula of Pd/C and a balloon of $H_2$ were used to reduce the nitrocarbazole to the amino carbazole. This was dissolved in 5 mL DMF and 0.167 g (0.75 mmol) N—Ac-L-Tyr, 0.394 g (0.96 mmol) HBTU and 0.19 mL (1.12 mmol) DIPEA were added. This was stirred for 1 h, diluted with ethyl acetate and washed consecutively with 0.1N $H_2SO_4$, aq. $NaHCO_3$ and brine and then dried over $Na_2SO_4$ and concentrated. Without purification this was dissolved in 5 mL THF and 5 mL water and 0.063 g (1.49 mmol) LiOH was added. The ester was cleaved in <20 min and diluted with ethyl acetate and washed consecutively with 0.1N $H_2SO_4$, and brine. This was dried over $Na_2SO_4$ and concentrated and then lyophilized and purified by HPLC.

EXAMPLE 5

Synthesis of Compound 8

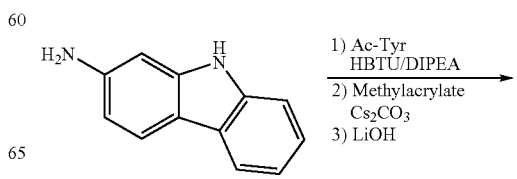

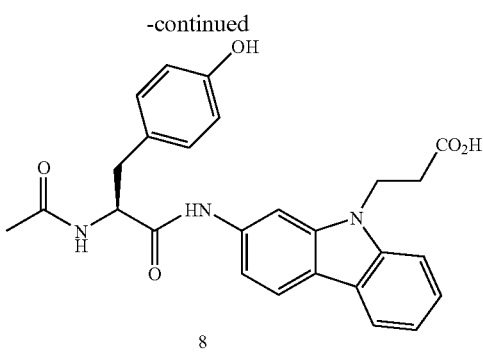

8

To 0.3 g (1.64 mmol) 2-aminocarbazole in 6 mL DMF was added 1.2 g (6.59 mmol) of the constrained-N—Ac-L-Tyr, 2.31 g (6.1 mmol) HBTU and 2 mL (11.5 mmol) DIPEA. The reaction was stirred for 2.5 h, poured into ethyl acetate and washed consecutively with 0.1N $H_2SO_4$, aq. $NaHCO_3$ and brine and then dried over $Na_2SO_4$ and concentrated. Flash chromatography (10% methanol/methylene chloride) gave 0.60 g of the acetylated amine. 0.20 g of this was stirred for 1 h with cesium carbonate (0.349 g, 1.07 mmol) and ethyl bromoacetate (0.08 mL, 0.73 mmol) in 5 mL DMF which was then poured into ethyl acetate and washed with saturated $NH_4Cl$ and brine and then dried over $Na_2SO_4$ and concentrated. Without purification this was dissolved in 4 mL THF and 4 mL water and 0.082 g (1.95 mmol) LiOH was added. The ester was cleaved in <30 min and then diluted with ethyl acetate and washed consecutively with 0.1N $H_2SO_4$, and brine. This was then dried over $Na_2SO_4$, concentrated and then lyophilized and purified by HPLC.

EXAMPLE 6

Synthesis of Compound 9

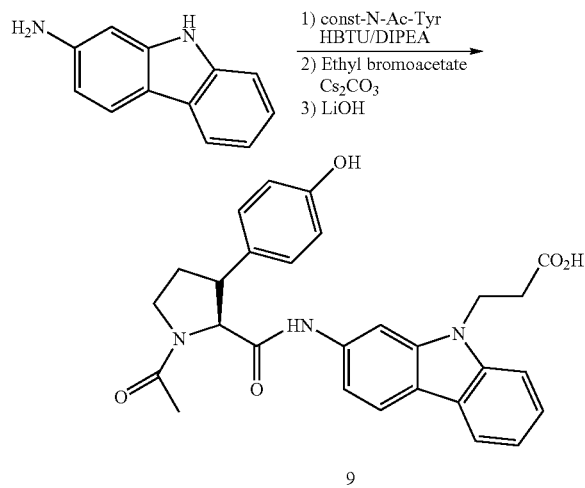

9

To 0.2 g (0.48 mmol) of the 2-aminocarbazole acylated by the constrained-Tyr (as in example 5) in 5 mL DMF was added cesium carbonate (0.349 g, 1.07 mmol) and methylacrylate (0.043 mL, 0.73 mmol). This was stirred for 1 h, then poured into ethyl acetate and washed with saturated $NH_4Cl$ and brine and then dried over $Na_2SO_4$ and concentrated. Without purification this was dissolved in 3 mL THF and 3 mL water and 0.081 g (1.92 mmol) LiOH was added. The ester was cleaved in <20 min and then diluted with ethyl acetate and washed consecutively with 0.1N $H_2SO_4$, and brine. This was dried over $Na_2SO_4$, concentrated and then lyophilized and purified by HPLC.

EXAMPLE 7

Synthesis of 3-amino-dibenzosuberol

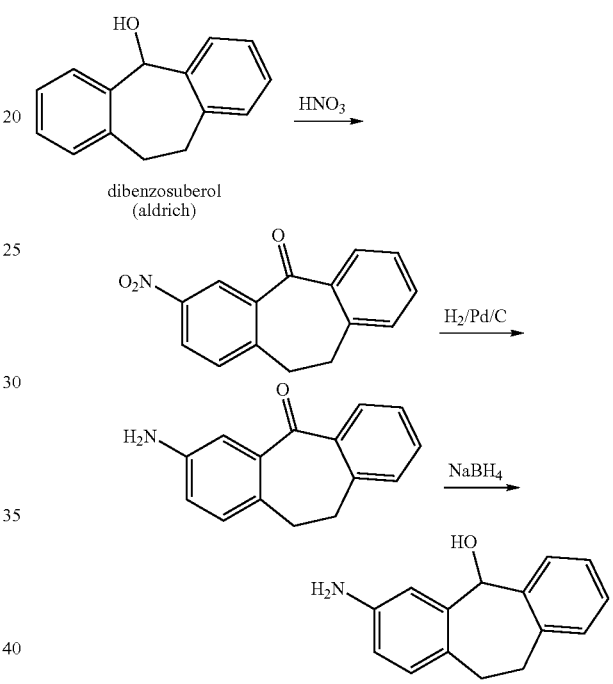

Dibenzosuberol (6.0 g, aldrich) was added to 100 ml of stirred concentrated nitric acid at ambient temperature. Periodic reaction progress analysis (tlc, NMR and IR) indicated that dibenzosuberol was first oxidized to dibenzosuberone, then nitrated at the 3-position. After 2 hours, the reaction mixture was poured into ice water and extracted with 1:1 hexane:ethyl acetate. The crude product was purified by flash chromatography on silica (9:1 hex/EtOac) to yield 3.22 g (45%) of 3-nitrodibenzosuberone. 3-nitrobenzosuberone (3.22 g) was reduced with hydrogen at 40 psi in 1:1 methanol/THF (40 ml), acetic acid (2 ml) and 10% Pd/C (0.5 g) for 1.5 hours. Filtration and concentration gave 3-aminodibenzosuberone 1.35 g (48%).

3-aminodibenzosuberone (1.35 g) and sodium borohydride (3 g) were dissolved in 100 ml THF. Ethanol (30 ml) was added in portions over one hour with stirring at ambient temperature. After 18 hours, 1N HCl was added dropwise until a pH of 7 was obtained. The reaction mixture was partitioned between 1:1 hexane/ethyl acetate and saturated aqueous sodium bicarbonate, washed with brine, dried over sodium sulfate, filtered and concentrated to give 11.0 g of crystalline 3-aminodibenzosuberol (74%).

EXAMPLE 8

Synthesis of Compound 10

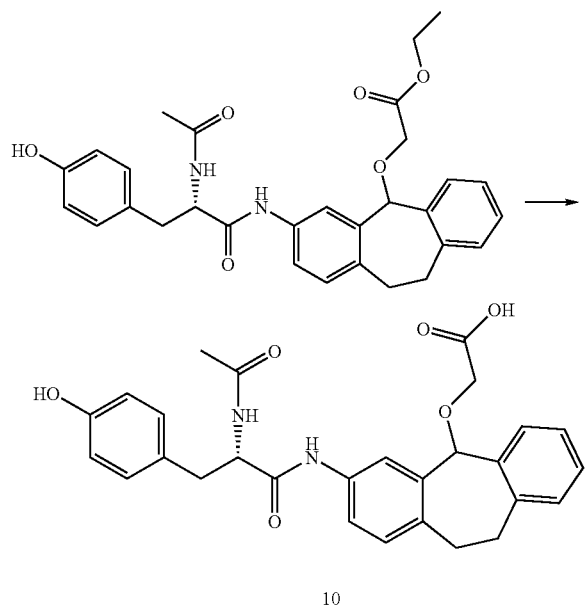

10

3-aminodibenzosuberol (0.95 g) was dissolved in dry DMF (10 ml). Sodium hydride (0.25 g of 60% in oil) was added and the reaction mixture stirred until hydrogen evolution ceased. Ethyl iodoacetate (1.35 g) was added and the reaction mixture stirred at ambient temperature for 3 hours then partitioned between ethyl acetate and water, washed with brine, dried and concentrated. Flash chromatography on silica (75:25, hex:EtOAc) gave 0.79 g of 3-amino-5-(ethyl carboxymethyl) dibenzosuberane (60%).

3-amino-5-(ethyl carboxymethyl) dibenzosuberane (395 mg), N-acetyl tyrosine (425 mg), HBTU (723 mg), diisopropylethylamine (491 mg) and 5 ml anhydrous DMF were combined and stirred at ambient temperature overnight. The reaction was partitioned between ethyl acetate and 10% aqueous citric acid. The organic phase was dried, filtered and the product purified on silica (96:4 methylene chloride:methanol) to give 290 mg of 24015-94.

The above product (24015-94, 50 mg) was dissolved in 8 ml of 1:1 ethanol:water and 6.1 mg of lithium hydroxide monohydrate added. After 3 hours, hydrolysis was complete and 1 ml of acetic acid was added. The reaction mixture concentrated and the product purified by HPLC (1 inch C-18, 10 to 90 in 60 min, 254 nm).

EXAMPLE 9

Synthesis of Compound 11

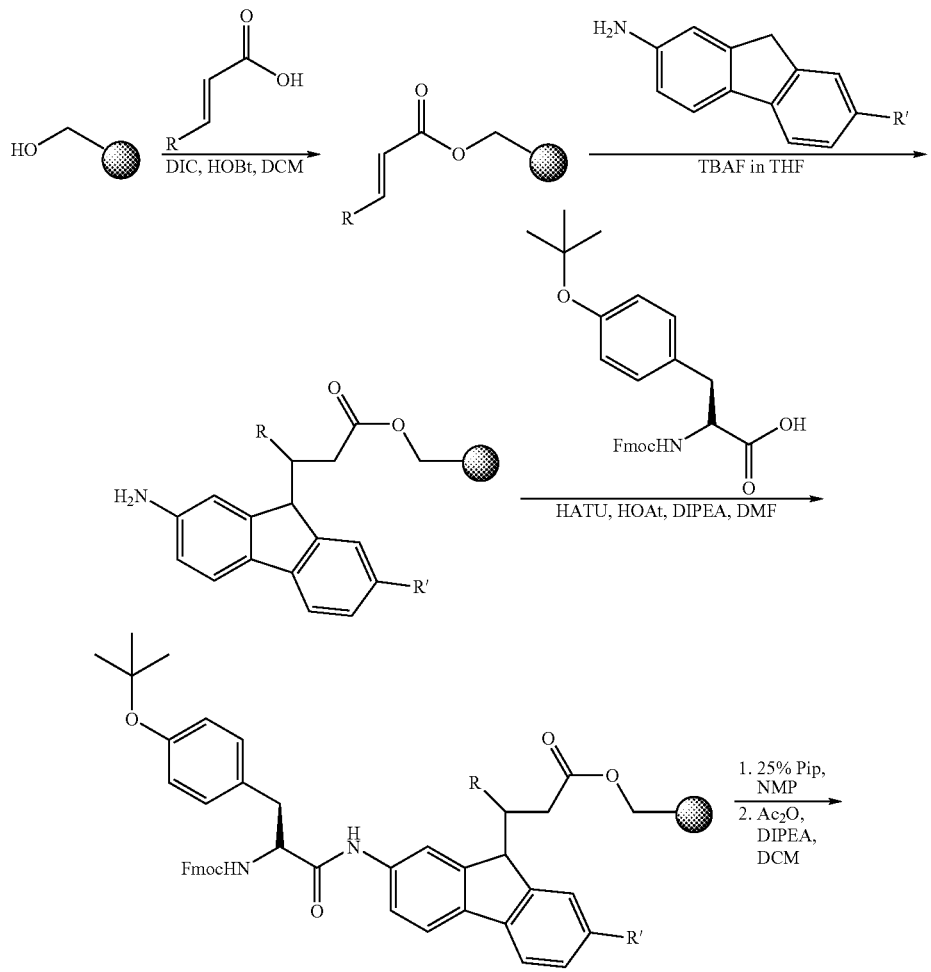

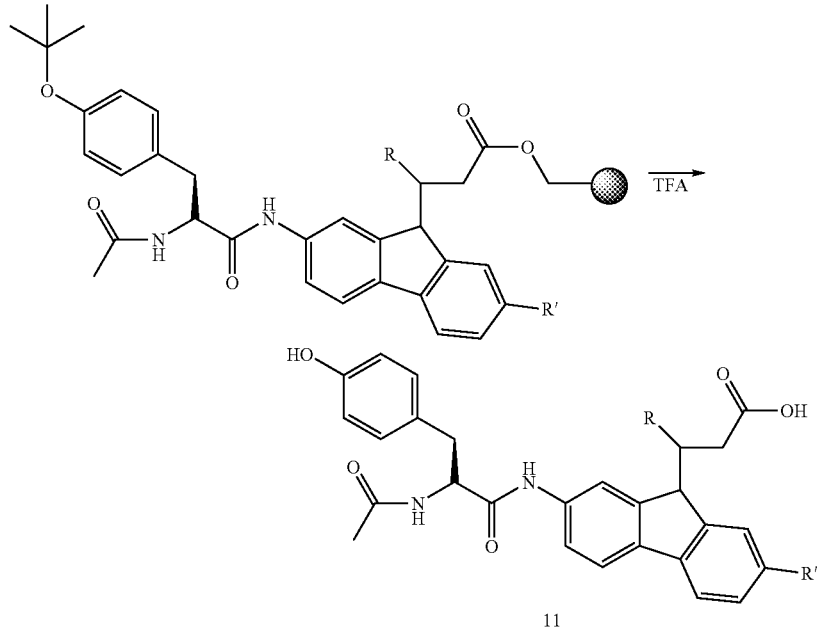

11

68 µL of acrylic acid (0.25 mmol, R=H) was added to 4 mL of DCM followed by 135 mg of HOBt (0.25 mmol) and 157 µL of DIPC (0.25 mmol). After equilibration for 2 min this solution was combined with 200 mg of Wang polystyrene resin (0.5 mmol/g, 0.1 mmol) and allowed to shake for 4 h at which time the resin was filtered and washed extensively with repeating volumes of DMF, THF, MeOH, and DCM. In a dry vial, 2 mL of THF was combined with 2 mL of a 1.0 M solution of TBAF in THF (Aldrich Chemical Company). 362.5 mg of 2-aminofluorene (X=H) was added to the TBAF solution and allowed to shake for 10 min. prior to adding it to the previously mentioned resin. The resin was stirred for 16 h and the washed as before. At this point, the amino acid tyrosine was coupled to the aniline on the fluorenyl ring by treating the resin with 4 mL of a 0.25 M solution of the amino acid, HOAt, HATU, and DIPEA in DMF for 16 h. After washing the resin the FMOC protecting group was removed by mixing the resin with 4 mL of a 25% piperidine solution in NMP for 10-15 min. The piperidine was removed from the resin with repeated washings and the acylation was performed on the resin using a solution of acetyl anhydride and DIPEA each at a 0.25 M concentration in 4 mL of DCM for 1 h, followed by a washing step. The compound was liberated from the resin by treating it with 4 mL of a 90% TFA, 5% DCM, 2.5% water and 2.5% triethylsilane cocktail for 1 h. The TFA solution was filtered from the resin and evaporated under a stream of nitrogen gas. The product was purified on a C-18 reversed phase HPLC to yield 3 mg of product (R, R'=H) and confirmed by mass spectroscopy.

The reaction with the acrylate could also be performed where R was an alkyl group. In cases where R'=Br then Suzuki couplings using aryl boronic acids were performed prior to the acylation with FMOC-tyrosine. A typical procedure is as follows. The resin (100 mg) is swelled in 2 mL NMP containing 0.25 M boronic acid, 0.25 M DIPEA, and 50 mg of Palladium catalyst, $Pd(PPh_3)_2Cl_2$ and heated to 60° C. for 6 hours. A variety of amine or carbonate bases and paladium catalysts could be also used to perform this transformation. Additionally the nitrogen on the tyrosine ring could be acylated or sulfonylated under a variety of conditions to yield products with functional groups other than the acetyl group. By products resulting from an additional acrylate adding to the 9-position of the fluorenyl ring were observed with higher loading resins and in some cases were isolated in significant quantities.

EXAMPLE 10

Biological Activity Assays

The compounds of the invention can be assayed for ability to block the $\alpha_4\beta_7$/MAdCAM-1 or $\alpha_4\beta_1$/VCAM-1 binding interaction by addition of serial dilutions of the samples to plates with the receptors as follows. 96-well plates are coated with mouse anti-human $\alpha_4$ (31470D, PharMingen, San Diego, Calif.). The plates are decanted and blocked with 0.5% BSA. After washing $\alpha_4\beta_1$ or $\alpha_4\beta_7$ is added, followed by incubation for 2 h at room temperature. The plates are washed and samples of the small molecule antagonists are added to the plates with MAdCAM-1-Ig-HRP or VCAM-1-Ig-HRP for 2 h at room temperature. After an additional wash, the bound MAdCAM-1-Ig-HRP or VCAM-1-Ig-HRP is detected by addition of tetramethylbenzidine (TMB, Kirkegaard & Perry, Gaithersberg, Md.), followed by detection of the absorbance of the product.

Alternatively, the compounds can be assayed using any known protein-protein or cell-based assay method, such as those described, for example, in WO 99/10312 (examples 179-180) and WO 99/36393 (RPMI-CS-1 cell adhesion assay). See also Cardarelli et al., 1994, J. Biol. Chem., 269:18668-18673.

For example, 96-well ELISA plates are coated overnight at 4° C. with 2 µg/ml with anti-human CD49d, (31470D, PharMingen, San Diego, Calif.) in phosphate buffered saline. The plates are decanted and blocked with assay buffer (50 mM Tris-HCl, pH 7.5, 150 mM NaCl, 1 mM MnCl$_2$, 0.05% Tween-20 and 0.5% BSA) at room temperature for one hour, with gentle shaking. The plates are washed three times (in 50 mM Tris-HCl, pH 7.5, 100 mM NaCl, 1 mM MnCl$_2$, 0.05% Tween-20) and 2 µg/ml of the desired integrin in assay buffer is added, followed by incubation at room temperature for two hours, with gentle shaking. After washing three times, 50 µl of samples of the small molecule antagonists (serial dilutions from 10 mM stocks in 100% DMSO) are added to the plates with 50 µl of 1 µg/ml MAdCAM-1-Ig-HRP or VCAM-1-Ig-HRP in assay buffer. The plates are incubated two hours at room temperature, with gentle shaking, followed by washing six times. The bound MAdCAM-1-Ig-HRP or VCAM-1-Ig-HRP is detected by addition of the peroxidase substrate, 3, 3', 5, 5', tetramethylbenzidine (TMB, Kirkegaard & Perry, Gaithersberg, Md.), for 10 minutes, followed by addition of 1M phosphoric acid to stop the reaction. The absorbance of the solutions are read at 450 nm on a plate reader.

Suitable animal models exist for many diseases and conditions which can be treated with the compounds of the invention. Additional confirmation of the efficacy of these compounds in specific diseases and at desired doses can be assayed using these established models. For example, animal models of chronic inflammatory diseases such as asthma (Laberge, S. et al., Am. J. Respir. Crit. Care Med., 1995, 151:822-829.), rheumatoid arthritis (RA; Barbadillo, C. et al., Springer Semin. Immunopathol., 1995, 16:375-379), and inflammatory bowel diseases (IBD; Podalski, D. K., N. Eng. J. Med., 1991, 325:928-937; Powrie, F. et al., Ther. Immunol., 1995, 2:115-123) may be used to demonstrate the activity of the compounds of the invention and to conduct dose and efficacy studies.

We claim:

1. A method of treating a disease or condition in a mammal wherein said disease or condition is selected from the group consisting of rheumatoid arthritis, asthma, psoriasis, multiple sclerosis, inflammatory bowel disease, Celiac disease, nontropical Sprue, graft-versus-host disease, pancreatitis, insulin-dependent diabetes mellitus, mastitis, cholecystitis, pericholangitis, chronic sinusitis, chronic bronchitis, pneumonitis, collagen disease, eczema, or systemic lupus erythematosis, said method comprising administering to said mammal an effective amount of a compound of having the formula (I):

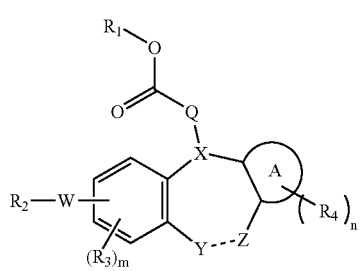

(I)

wherein

A is a 5 or 6 member, saturated or unsaturated carbocycle or heterocycle optionally substituted by oxo and $R_4$;

Q is alkyl, alkenyl or alkynyl optionally substituted with halogen, carboxyl, alkyl or aryl, and wherein one or more carbon atoms are optionally replaced with O, N, NR$_6$, S, SO, or SO$_2$;

X is —CR$_5$— or —N—;

Y is H, —CHR$_3$—, —CR$_3$=, or a bond;

Z is H, CHR$_3$—, =CR$_3$—, —NR$_3$—, =N—, O, S, SO, SO$_2$ or a bond, provided that when one of Y and Z is H then the other is also H;

W is —C(O)NR$_6$—, —NR$_6$C(O)—, —C(S)NR$_6$—, —NR$_6$C(S)—, NR$_6$, O, S, SO$_2$, —CH$_2$—, —C—, —NR$_6$SO$_2$—, —SO$_2$NR$_6$—, —OC(O)NR$_6$—, —NR$_6$C(O)O—, —OC(S)NR$_6$—, —NR$_6$C(S)O—, —S—C(S)NR$_6$—, —C(O)—, —NR$_6$C(O)NR$_6$— or —NR$_6$C(S)NR$_6$—;

R$_1$ is hydrogen or is selected from the group consisting of alkyl, alkenyl and alkynyl, each of which is optionally substituted with hydroxyl, halogen, amino, nitro, carboxyl, a carbocycle, or a heterocycle; or R$_1$ is a carbocycle or heterocycle optionally substituted with hydroxyl, oxo, halogen, amino, or nitro;

R$_2$ is selected from the group consisting of alkyl, alkenyl and alkynyl, each of which is optionally substituted with halogen, hydroxyl, oxo, alkoxy, amino, nitro, carboxyl, carboxamido, acyl, acyloxy, amidinyl, guanidinyl, thiol, alkylthio, or one or more carbocycle or heterocycle optionally substituted with halogen, hydroxyl, oxo, alkoxy, amino or carboxyl; or R$_2$ is a carbocycle or heterocycle optionally substituted with halogen, hydroxyl, oxo, alkoxy, amino, nitro, carboxyl, acyl, acyloxy, alkyl, alkenyl, alkynyl or a carbocycle or heterocycle optionally substituted with halogen, hydroxyl, oxo, alkoxy, amino or carboxyl;

R$_3$ and R$_4$ are independently selected from the group consisting of H, hydroxyl, halogen, amino, nitro, carboxyl, alkyl, alkenyl, alkynyl, a carbocycle and a heterocycle, wherein said alkyl, alkenyl, alkynyl, carbocycle and heterocycle groups are optionally substituted with one or more substituents selected from the group consisting of hydroxyl, halogen, amino, oxo and carboxyl, and optionally one or more carbon atoms of said alkyl, alkenyl and alkynyl group is replaced with N, NR$_6$, O, S, SO or SO$_2$;

R$_5$ is H or alkyl, alkenyl or alkynyl optionally having a carbon atom replaced with O, N or NR$_6$, and optionally substituted with COOR$_1$; or R$_5$ together with the carbon atom from which it depends forms a double bond to an adjacent carbon or nitrogen atom of Q; or R$_5$ together with a nonadjacent carbon or nitrogen atom of Q form a carbocycle or heterocycle;

R$_6$ is hydrogen, alkyl, alkenyl or alkynyl;

m and n are independently 1, 2 or 3;

and salts, solvates and hydrates thereof.

2. The method according to claim 1, wherein A is a benzene ring.

3. The method according to claim 1, wherein Q is a alkyl chain of 1 to 3 carbon atoms in length wherein the methylene group adjacent to X is optionally replaced with oxygen.

4. The method according to claim 3, wherein said methylene chain is 2 carbon atoms in length.

5. The method according to claim 4, wherein the methylene group adjacent to X is replaced with oxygen.

6. The method according to claim 1, wherein R$_1$ is H.

7. The method according to claim 1, wherein X is —CR$_5$— and R$_5$ is H.

8. The method according to claim 1, wherein both Y and Z are hydrogen.

9. The method according to claim 1, wherein both Y and Z are a bond thereby forming a 5 member ring with X.

10. The method according to claim 1, wherein W is —NR$_6$— and R$_6$ is H or C$_{1-4}$ alkyl.

11. The method according to claim 1, wherein $R_2$ is a D or L-amino acid residue wherein the alpha amino group is optionally an acyl group.

12. The method according to claim 11, wherein said amino acid is tyrosine.

13. The method according to claim 10, wherein $R_2$ is N-acetyl-tyrosine, D-tyrosine, phenylalanine, benzoyl, isonipecotoyl, 4-methoxyphenylacetyl, 1-fluorenyl-carbonyl, 1-naphthoyl, 2-naphthoyl, 3-hydroxy-phenylalanine, 3-iodo-tyrosine, 3-fluoro-tyrosine, 3-chloro-tyrosone, 4-(4-hydroxyphenyl)-benzoyl, 2,3,5,6-tetrafluoro-tyrosine, 6-hydroxynaphthoyl, 2-phenyl-3-(4-hydroxyphenyl)propanoyl and N-acetyl-3-(4-hydroxyphenyl)proline.

14. The method according to claim 1 having the formula (II):

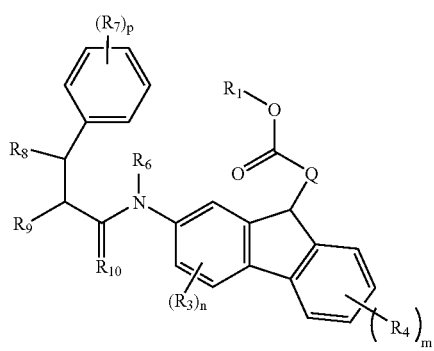

wherein
- Q is alkyl, alkenyl or alkynyl optionally substituted with halogen, carboxyl, alkyl or aryl, and wherein one or more carbon atoms are optionally replaced with O, N, $NR_6$, S, SO, or $SO_2$;
- $R_1$ is hydrogen or is selected from the group consisting of alkyl, alkenyl and alkynyl, each of which is optionally substituted with hydroxyl, halogen, amino, nitro, carboxyl, a carbocycle, or a heterocycle; or $R_1$ is a carbocycle or heterocycle optionally substituted with hydroxyl, oxo, halogen, amino, or nitro;
- $R_3$ and $R_4$ are independently selected from the group consisting of H, hydroxyl, halogen, amino, nitro, carboxyl, alkyl, alkenyl, alkynyl, a carbocycle and a heterocycle, wherein said alkyl, alkenyl, alkynyl, carbocycle and heterocycle groups are optionally substituted with one or more substituents selected from the group consisting of hydroxyl, halogen, amino, oxo and carboxyl, and optionally one or more carbon atoms of said alkyl, alkenyl and alkynyl group is replaced with N, $NR_6$, O, S, SO or $SO_2$;
- $R_6$ is hydrogen, alkyl, alkenyl or alkynyl;
- $R_7$ is hydrogen; hydroxyl, halogen, alkyl, alkoxy or halogen substituted alkyl;
- $R_8$ is H, alkyl, alkenyl or alkynyl;
- $R_9$ is H or $NR_{11} R_{11'}$ wherein $R_{11}$ and $R_{11'}$ are independently H, acyl or and amino acid residue; or one of $R_{11}$ and $R_{11'}$ together with $R_8$ form a heterocycle;
- $R_{10}$ is O or S;
- m and n are independently 1, 2 or 3;
- p is an integer from 1 to 5;
- and salts, solvates and hydrates thereof.

15. The method according to claim 14, wherein one of $R_{11}$ and $R_{11'}$ together with $R_8$ form a 5-member heterocycle while the other of $R_{11}$ and $R_{11'}$ is H or $C_{1-4}$ alkanoyl.

16. The method according to claim 15, wherein $R_5$ is OH at the para position.

17. The method according to claim 1 selected from the group consisting of

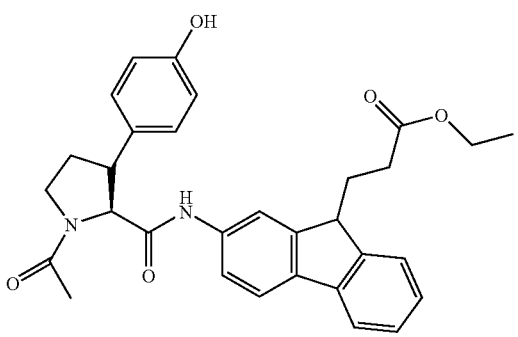

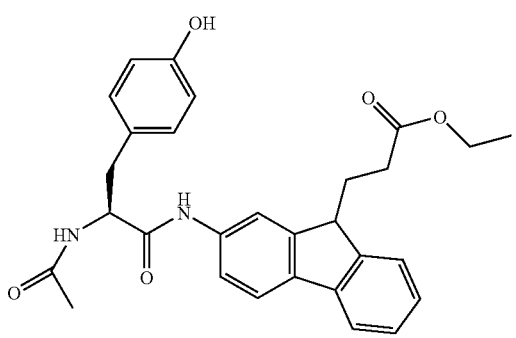

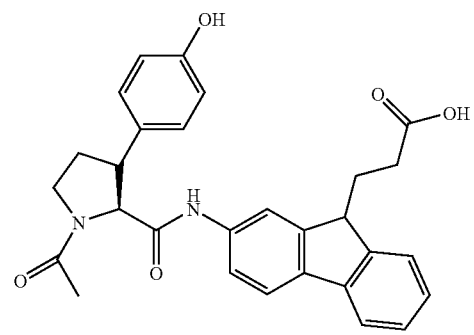

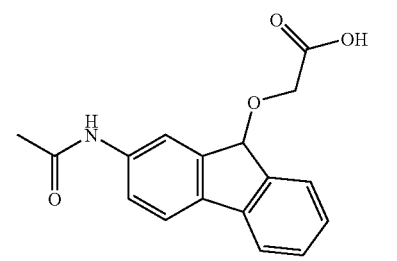

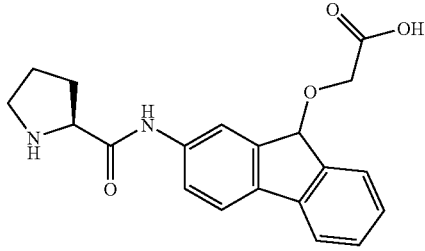

-continued
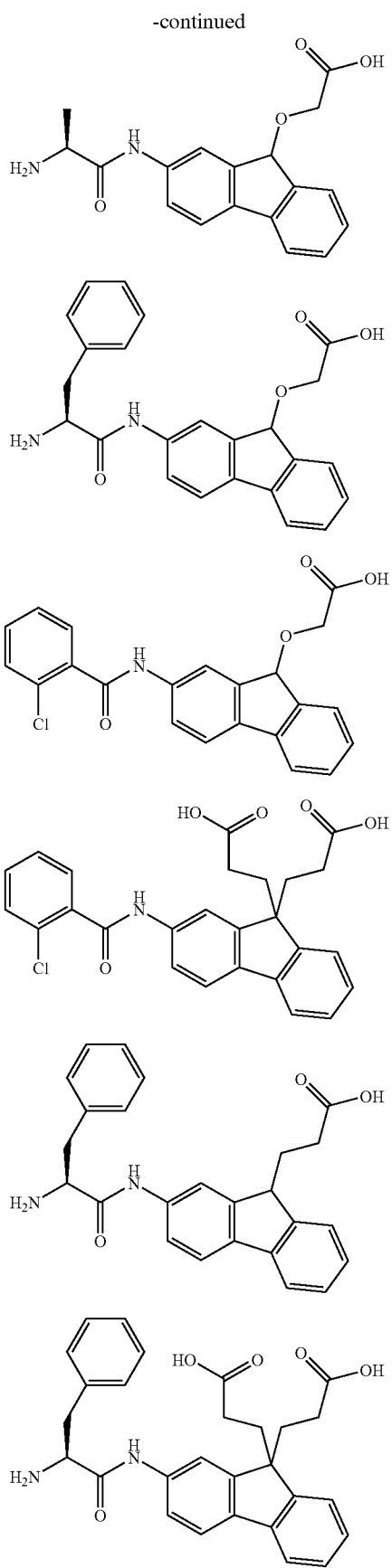
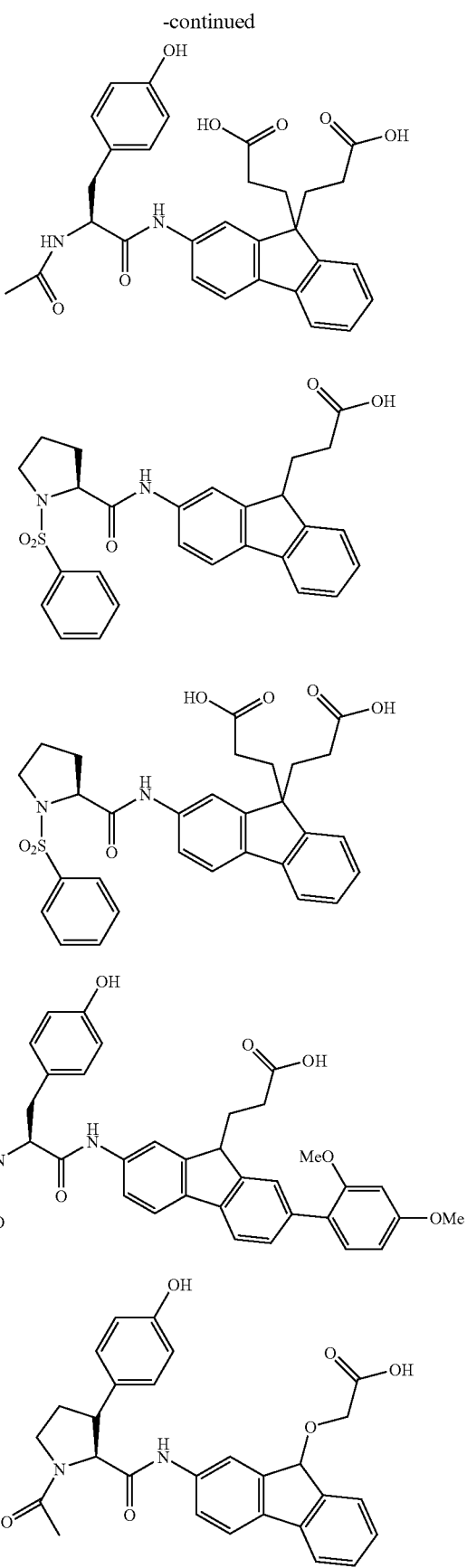

-continued
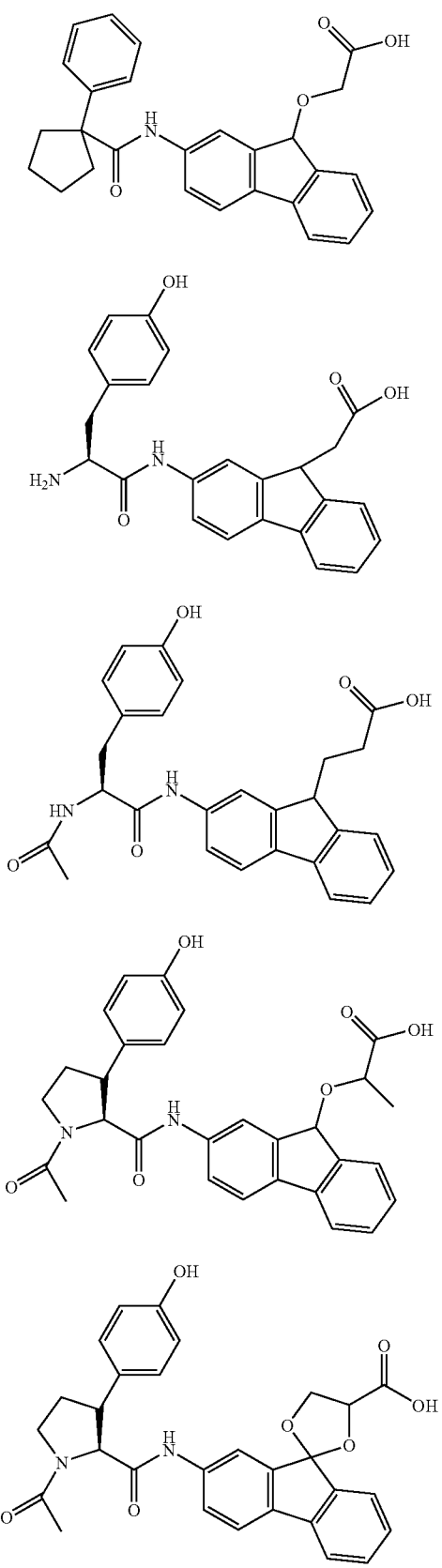
-continued
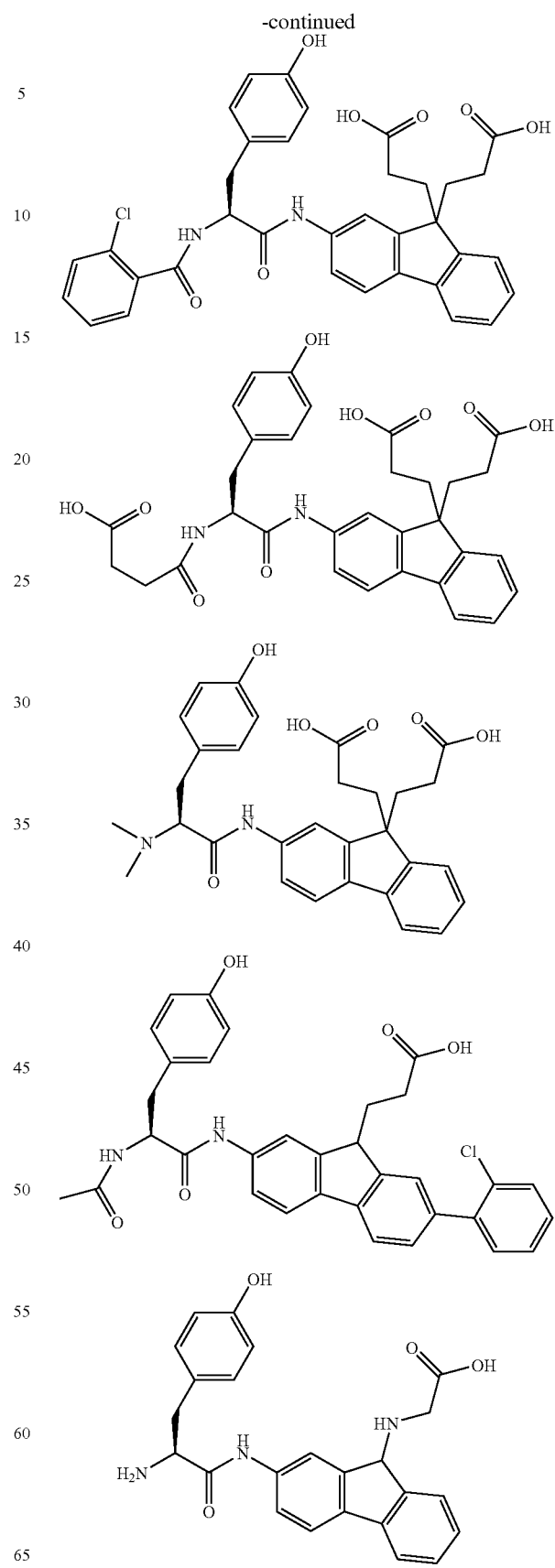

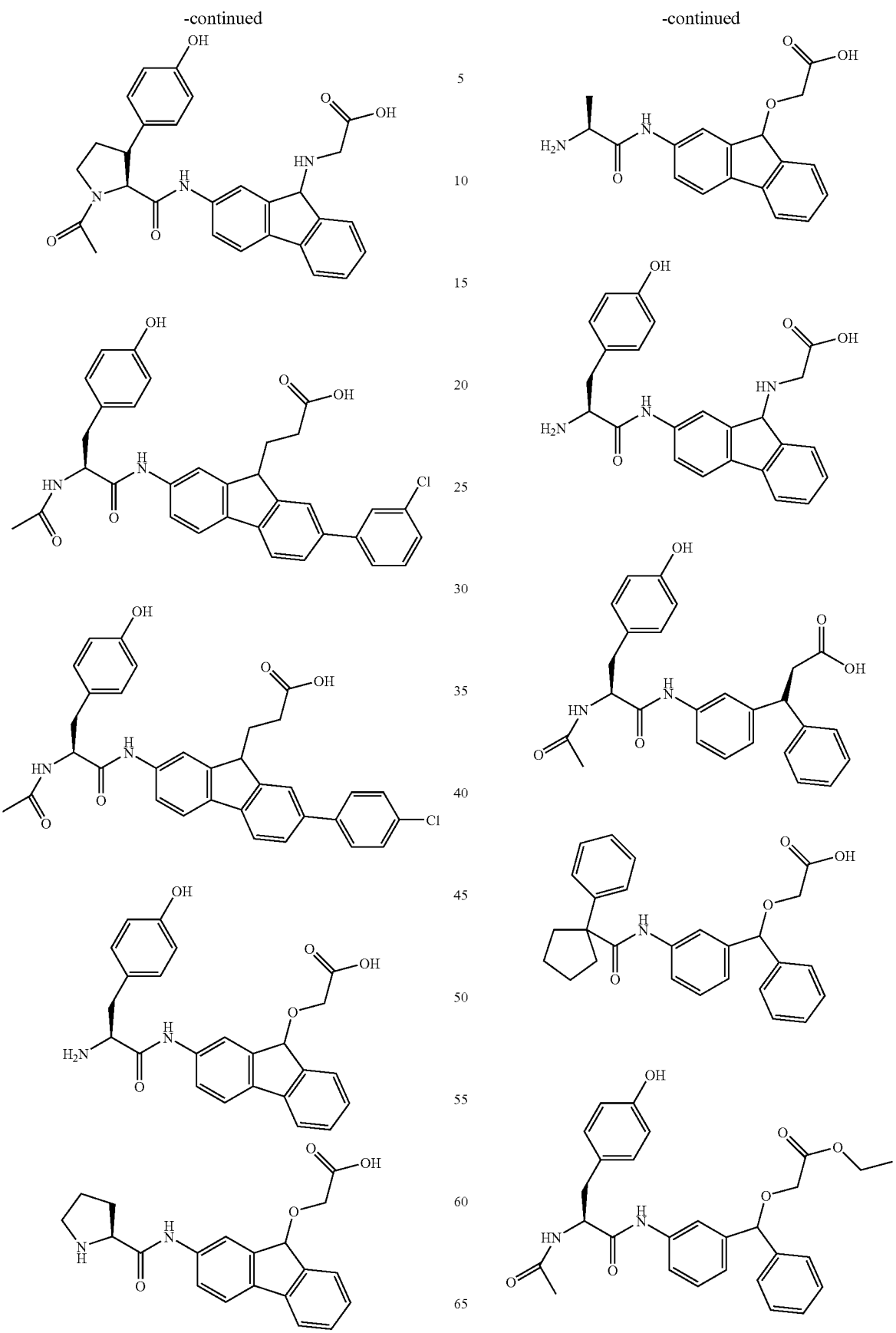

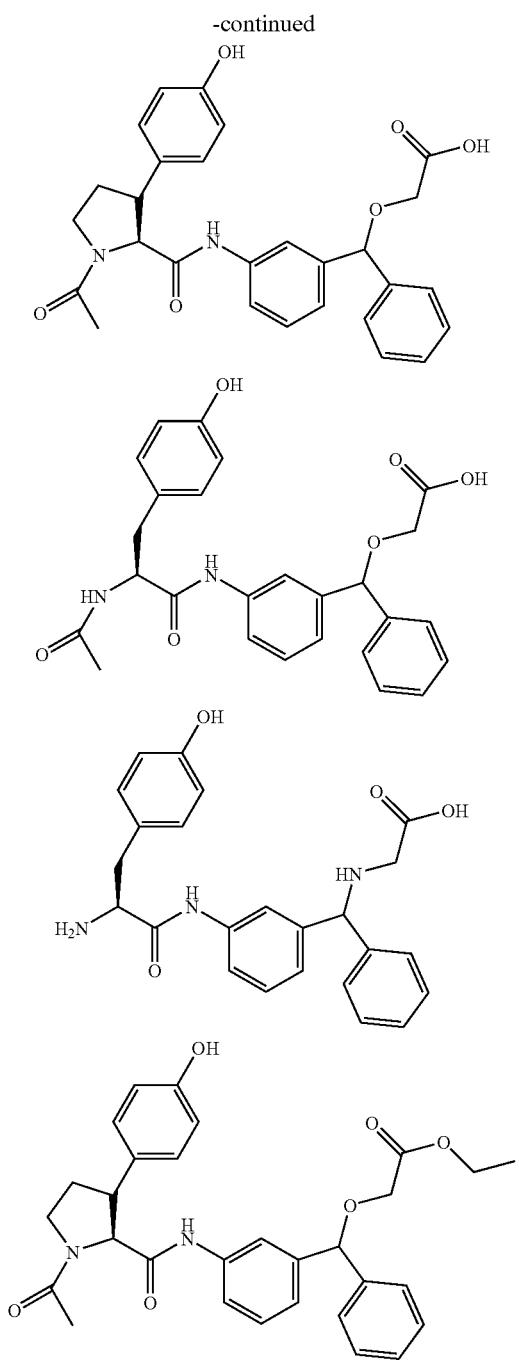
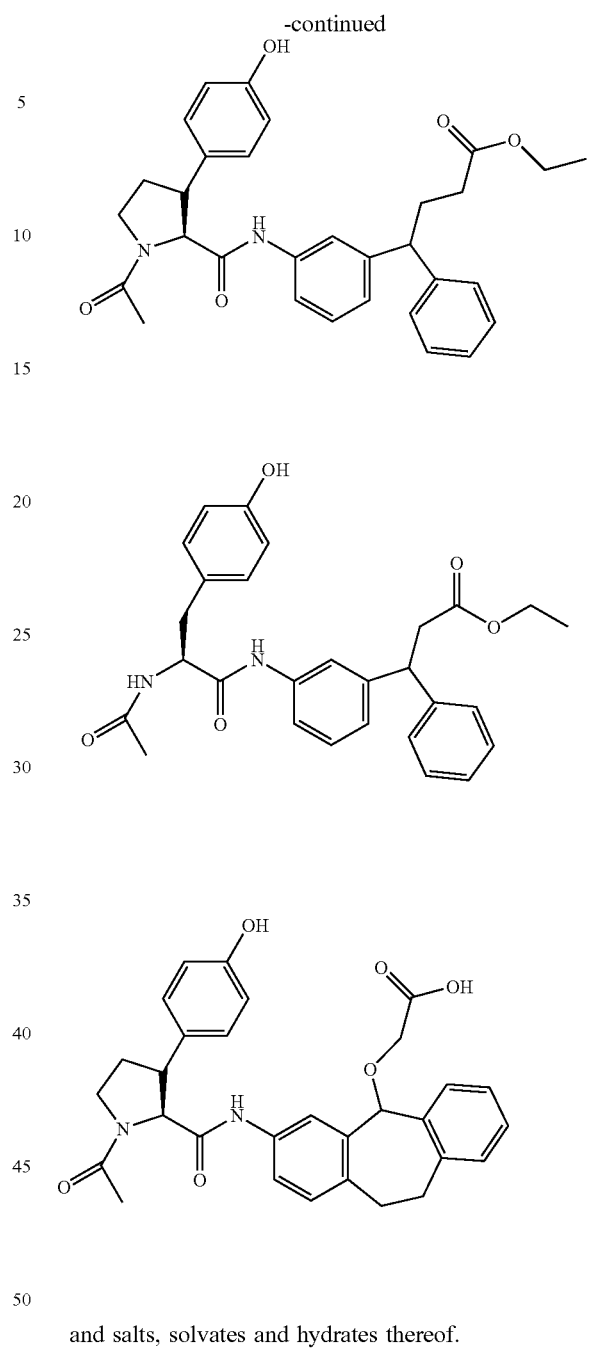
and salts, solvates and hydrates thereof.
* * * * *